(12) United States Patent
Nataraj et al.

(10) Patent No.: US 9,272,004 B2
(45) Date of Patent: Mar. 1, 2016

(54) STABILIZED, STERILIZED COLLAGEN SCAFFOLDS WITH ACTIVE ADJUNCTS ATTACHED

(75) Inventors: Chandrasekaran Nataraj, Gainesville, FL (US); Gregg Ritter, Gainesville, FL (US); Thomas Sander, Gainesville, FL (US)

(73) Assignee: Synovis Orthopedic and Woundcare, Inc., St. Paul, MN (US)

( * ) Notice: Subject to any disclaimer, the term of this patent is extended or adjusted under 35 U.S.C. 154(b) by 879 days.

(21) Appl. No.: 12/827,896

(22) Filed: Jun. 30, 2010

(65) Prior Publication Data
US 2010/0266559 A1 Oct. 21, 2010

Related U.S. Application Data

(63) Continuation of application No. 11/686,859, filed on Mar. 15, 2007, now abandoned.

(60) Provisional application No. 60/743,542, filed on Mar. 17, 2006.

(51) Int. Cl.
| | |
|---|---|
| *A61F 2/00* | (2006.01) |
| *A61K 9/14* | (2006.01) |
| *C07K 1/00* | (2006.01) |
| *A61K 35/32* | (2015.01) |
| *A61K 35/34* | (2015.01) |
| *A61K 35/36* | (2015.01) |
| *A61L 17/08* | (2006.01) |
| *A61L 27/36* | (2006.01) |
| *A61K 31/70* | (2006.01) |
| *A61F 2/28* | (2006.01) |
| *A61F 2/30* | (2006.01) |

(52) U.S. Cl.
CPC ............. *A61K 35/32* (2013.01); *A61K 35/34* (2013.01); *A61K 35/36* (2013.01); *A61L 17/08* (2013.01); *A61L 27/3683* (2013.01); *A61F 2/28* (2013.01); *A61F 2/30756* (2013.01); *A61F 2002/2817* (2013.01); *A61F 2002/30677* (2013.01); *A61F 2002/30766* (2013.01); *A61F 2310/00359* (2013.01); *A61F 2310/00365* (2013.01)

(58) Field of Classification Search
CPC .... A61K 35/32; A61L 17/08; A61L 27/3683; A61L 27/3687
USPC .................................. 424/426, 484
See application file for complete search history.

(56) References Cited

U.S. PATENT DOCUMENTS

| | | | | |
|---|---|---|---|---|
| 4,378,224 | A * | 3/1983 | Nimni et al. | 8/94.11 |
| 5,702,818 | A * | 12/1997 | Cahalan et al. | 428/409 |
| 6,117,979 | A * | 9/2000 | Hendriks et al. | 530/356 |
| 6,468,313 | B1 * | 10/2002 | Claeson et al. | 623/23.72 |
| 6,521,179 | B1 * | 2/2003 | Girardot et al. | 422/28 |
| 2006/0147492 | A1 * | 7/2006 | Hunter et al. | A61B 17/11 424/426 |

OTHER PUBLICATIONS

G.B. Oliveira et al., "Properties of carbodiimide treated heparin", Biomaterials, (2003) vol. 24, pp. 4777-4783.

* cited by examiner

*Primary Examiner* — Quang Nguyen
(74) *Attorney, Agent, or Firm* — James S. Keddie; Bret E. Field; Bozicevic, Field & Francis LLP

(57) ABSTRACT

Bioimplants and methods of making the bioimplants are provided. The bioimplants comprise biological tissues having conjugated thereto adjunct molecules. The biological tissues are sterilized with a chemical sterilizing agent, such as a water soluble carbodiimide. The processes of making the bioimplants include a process in which an adjunct molecule is conjugated to a biological tissue during the sterilization process.

9 Claims, 7 Drawing Sheets

Scheme 2A

Scheme 3A

FIG. 5A Control Pericardium
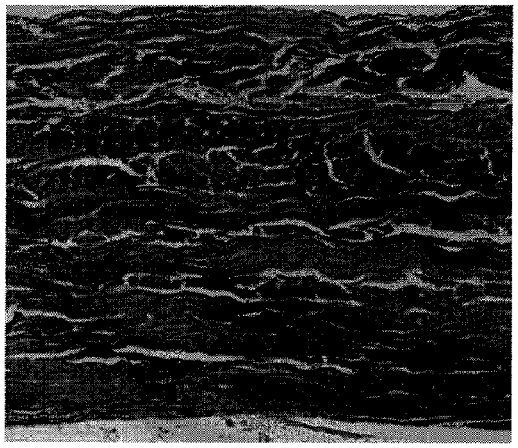
FIG. 5B Partial GAG Pericardium
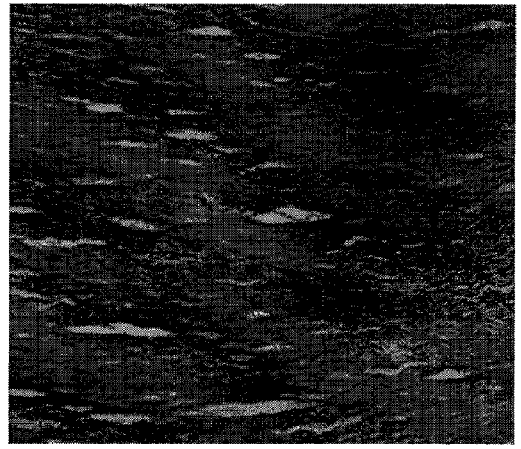
FIG. 5C Complete GAG Pericardium

FIG. 6A
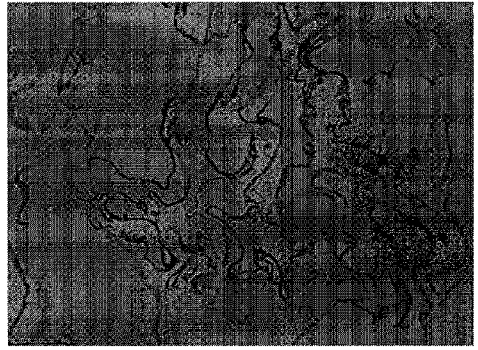
FIG. 6B
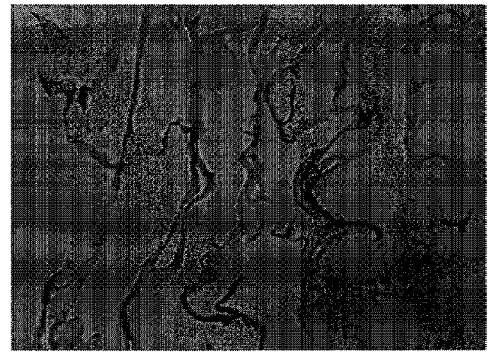
FIG. 7A  GAG-Cancellous Bone
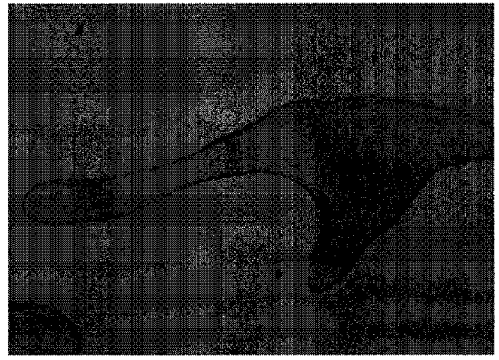
FIG. 7B  GAG-Type I Collagen Sponge
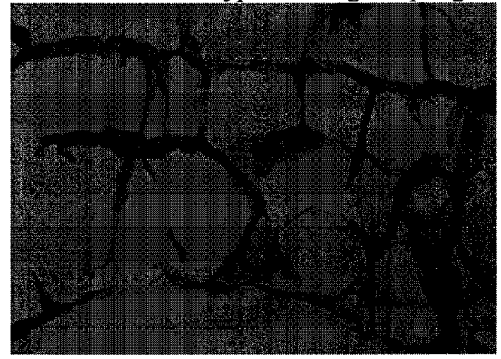
FIG. 8A  HA-Collagen Sponge
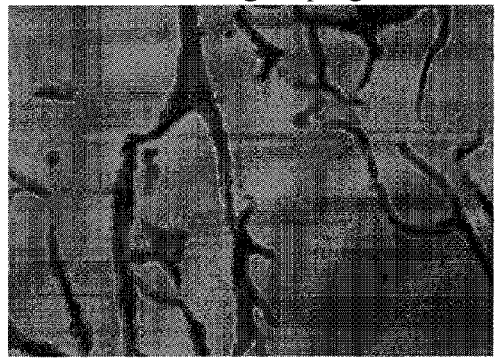
FIG. 8B  HA-Collagen Sponge
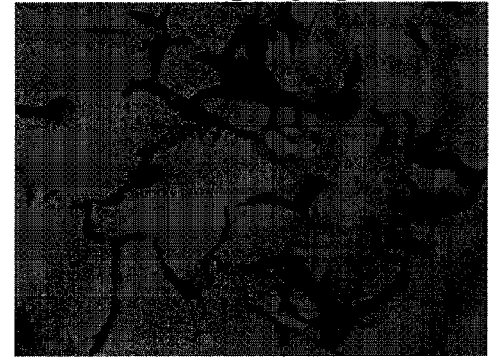

FIG. 8C HA-Pericardium
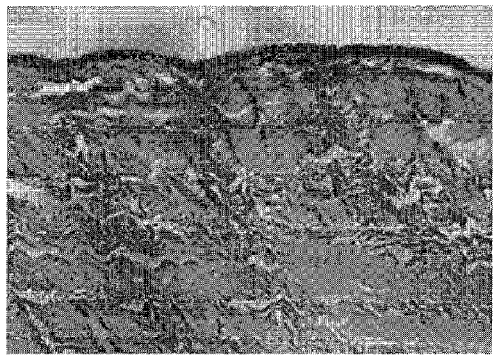
FIG. 8D IGF-1 Collagen Sponge
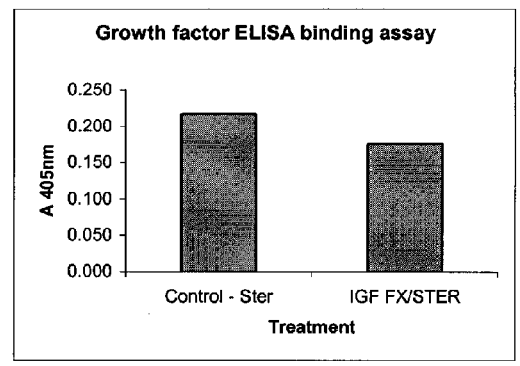
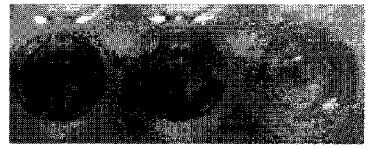
FIG. 9 – Cell Viability Assay (MTT Assay)
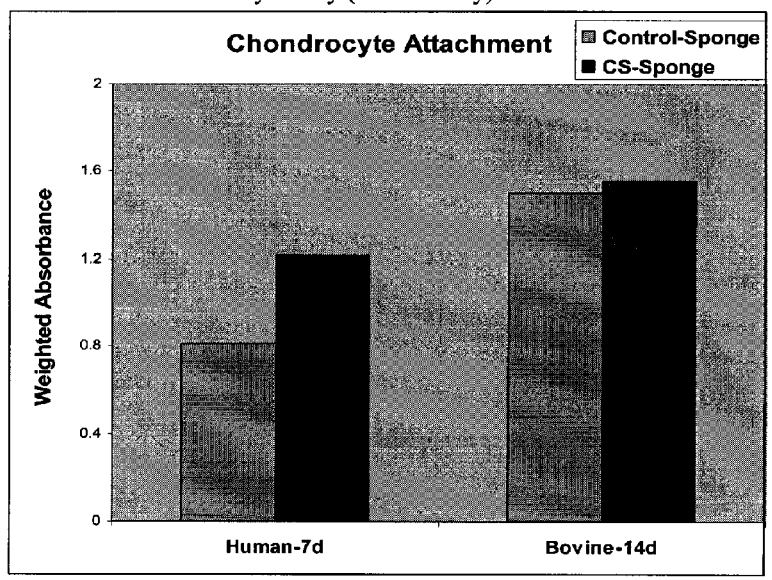

FIG. 10A GAG-Sponge+Cells (Lo Mag)
FIG. 10B GAG-Sponge + Cells (Hi Mag)
FIG. 10C GAG-Sponge + Cells (New Matrix)
FIG. 11A GAG-Sponge 1 month (PAS-AB)
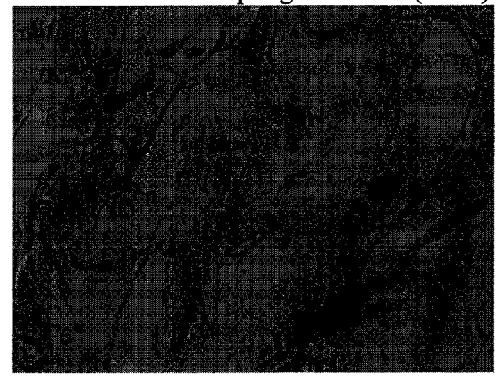
FIG. 11B GAG-Sponge 1 month (H&E)

STABILIZED, STERILIZED COLLAGEN SCAFFOLDS WITH ACTIVE ADJUNCTS ATTACHED

CROSS-REFERENCE TO RELATED APPLICATIONS

This application is a continuation of U.S. Ser. No. 11/686,859 filed Mar. 15, 2007, which is a non-provisional application of U.S. Ser. No. 60/743,542 filed on Mar. 17, 2006, the disclosures of which are incorporated by reference.

BACKGROUND OF THE INVENTION

Natural tissue bioimplants are gaining acceptance as advantageous alternatives to synthetic implants in many surgical procedures. Among other advantages, bioimplants more closely resemble in size, shape and performance the biological structures that they are designed to replace than do synthetic implants. Thus bioimplants are, in many circumstances, considered the devices of choice for replacement or structural augmentation of internal tissues and organs.

The sources of bioimplants include non-human and human donors. In general, the choice of donor depends on a number of factors, including the relative sizes of the donor and recipient. For example, as an alternative to a human cadaver, a sheep, pig, cow or horse may serve as a donor. In some cases, the donor and recipient may be the same. Immunogenic limitations are overcome by crosslinking the tissues to mask antigenic molecules in the tissue. Sterilization is generally effected by contacting the tissue with a chemical sterilizing agent. In many cases, crosslinked and sterilized bioimplants provide many of the features of natural tissue, while avoiding to a great degree the problem of xeno-tissue rejection that is characteristic of live tissue implantation.

In many cases, bioimplants provide additional advantages over synthetic implants. For example, many bioimplants permit infiltration of the recipient's own cells into the bioimplant. In particular, the infiltrating cells can use the bioimplant as a template or scaffold for re-constructing organ or tissue structures comprising the recipient's own cells. In some cases, all or part of the bioimplant can be replaced by the recipient body's own cells. This process, which is referred to as remodeling, is advantageous in that it can improve the integration of the bioimplant into the implant site. Due to these advantages, it is considered advantageous to promote remodeling of bioimplant tissue.

While some bioimplants can stimulate remodeling by themselves due to their natural origin and their possession of a collagen matrix that acts as a scaffold for tissue regrowth, it is sometimes considered advantageous to stimulate remodeling by administering to a bioimplant recipient one or more agents that stimulate tissue growth. For example, bone morphogenic proteins (BMPs) have been used experimentally to promote bone regrowth in spinal fusion surgery. For example, a resorbable collagen sponge infused with recombinant bone morphogenic protein-2 (rhBMP-2) has been approved for use in spinal surgery. It is believed that release of rhBMP-2 from the sponge stimulates osteoblast infiltration, proliferation and organization. As the collagen sponge is resorbable, eventually regrown host tissue replaces the sponge. The use of the rhBMP-2 infused collagen sponge in spinal surgery has been credited with greatly reducing the failure rate of spinal surgery.

Despite the improvements in surgical outcomes that have already been provided by growth factor infused bioimplants, many challenges remain to be overcome. For example, infusion of bioimplants is only useful where the bioimplant is absorbent, that is where soaking of the tissue in a solution containing the growth factor results in there being enough growth factor infused into the tissue to stimulate tissue growth after it has been implanted into a recipient. Thus, the infusion method is not considered effective for less porous bioimplant devices such as heart valves, skin grafts, tendon, bone and ligament repair tissues, etc. Another limitation is that release of the growth factor is by diffusion. While diffusion can in some instances be a useful method of release, in other circumstances diffusion may result in too high an initial rate of release and thus too low a later rate of release. Thus, one disadvantage of diffusive release is that the effective release period may be shorter than desired, unless excess growth factor is infused into the bioimplant at the start. However, this may not always be feasible or even possible. Moreover, even if it were possible to infuse excess growth factor into the bioimplant, a disadvantage arising out of this approach may be that the local concentration of growth factor may cause diffusion of the growth factor into surrounding tissue, including capillaries, veins and arteries, where it may bring about deleterious local or systemic effects. In some cases, such diffusion may even give rise to new tissue growth in an area distal to the area where new growth is desired.

There is thus a need for a device that overcomes the limitations of the prior art growth factor infused collagen sponge. There is a need for a bioimplant device that is capable of delivering growth factor to a desired area, wherein the growth factor is released from the bioimplant device at a rate that is less than the diffusive rate of release from the prior art growth factor-infused collagen sponge. There is likewise a need for a bioimplant device that has associated with it a growth factor that is subject to degradation of the growth factor to a lesser degree than is the growth factor-infused collagen sponge of the prior art. There is also a need for a bioimplant device that has associated with it a growth factor that is covalently bonded to the bioimplant. There is likewise a need for processes of making such bioimplant devices. These and other needs are met by embodiments of the invention.

There is also a need for a bioimplant device that carries an adjunct. There is also a need for a bioimplant device that is capable of delivering an adjunct to a desired area, wherein the adjunct is released from the bioimplant at a rate that is less than the diffusive rate of release of the adjunct from an infused collagen sponge. There is likewise a need for a bioimplant device that has associated with it an adjunct that is subject to degradation to a lesser degree than an adjunct in an adjunct-infused collagen sponge. There is also a need for a bioimplant device that has associated with it an adjunct molecule that is covalently bonded to the bioimplant. There is likewise a need for processes of making such bioimplant devices. These and other needs are met by embodiments of the invention.

SUMMARY OF THE INVENTION

The foregoing and further needs are met by embodiments of the invention, which provide a bioimplant comprising a chemically sterilized biological tissue and at least one adjunct, wherein the adjunct is covalently conjugated to the biological tissue. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

The foregoing and further embodiments are further met by embodiments of the invention, which provide a process of making the bioimplant, comprising: (a) contacting a biological tissue with an adjunct to form a combination; and (b) contacting the combination with a chemical sterilizing agent to form the bioimplant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

In some embodiments, the invention further meets the foregoing and related needs by providing a process of making a sterilized biological implant, comprising: (a) contacting a starting tissue with an adjunct to form an intermediate; (b) freezing the intermediate product of (a) to produce a frozen intermediate; (c) lyophilizing the frozen intermediate from (b) to produce a lyophilized intermediate; and (d) contacting the lyophilized intermediate with a sterilizing solution comprising a carbodiimide sterilizing agent to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

The invention further meets the foregoing and related needs by providing a process of making a sterilized biological implant, comprising: (a) preparing a composition comprising a starting tissue; (b) freezing the composition from (a) to form a frozen composition; (c) lyophilizing the frozen composition from (b) to form a lyophilized composition; and (d) contacting the lyophilized composition from (c) with a sterilizing solution comprising a sterilizing agent and an adjunct to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

In some embodiments, the invention meets the foregoing and further needs by providing a process of making a sterilized biological implant, comprising: (a) contacting a starting tissue with a crosslinking agent to at least partially crosslink the starting tissue to produce a crosslinked tissue; and (b) contacting the crosslinked tissue from (a) with a sterilizing solution comprising a sterilizing agent and an adjunct to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

The invention further addresses the foregoing and related needs by providing a process of making a sterilized biological implant, comprising: (a) contacting a starting tissue with a crosslinking agent and an adjunct to at least partially crosslink the starting tissue to produce a crosslinked tissue adjunct-conjugated tissue; and (b) contacting the crosslinked tissue from (a) with a sterilizing solution comprising a sterilizing agent to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol.

The invention further satisfies the foregoing and related needs by providing a process of making a sterilized biological implant, comprising: (a) contacting a starting tissue with a sterilizing solution comprising a sterilizing agent to produce a sterilized intermediate and; (b) contacting the sterilized intermediate from (a) with an adjunct to produce the biological implant; and (c) optionally subjecting the implant to another sterilization step. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. In some embodiments, the optional final sterilization step (c) is carried out in the presence of a water soluble carbodiimide, such as EDC. In other embodiments, another sterilization agent, such as glutaraldehyde, is used; while in still further embodiments the sterilization step (c) may be carried out with γ-irradiation or electron beam irradiation.

In some embodiments, the invention provides a bioimplant comprising a chemically sterilized biological tissue and at least one adjunct, wherein the adjunct is covalently conjugated to the biological tissue. In some embodiments, the chemically sterilized biological tissue is sterilized with a carbodiimide, such as EDC, optionally in the presence of an alkanol, such as a $C_2$-$C_4$ alkanol, especially isopropanol. In some embodiments, the chemically sterilized biological tissue is crosslinked with a carbodiimide, optionally in the presence of a bifunctional crosslinking agent. In some embodiments, the biological tissue comprises native tissue, processed tissue in native form, processed tissue in non-native form, a composite or a complex composite. In some embodiments, (1) said native tissue comprises bone, tendon, ligament, dermis, fascia, pericardium, and combinations thereof, including bone-connective tissue combinations, such as bone-tendon combinations and bone-ligament-bone combinations; (2) said processed tissue in native form comprises crosslinked tissue, decellularized crushed bone fragments, decellularized collagen or other decellularized and/or defatted bone, tendon, ligament, fascia or bone-connective tissue combinations, such as bone-ligament-bone or bone-tendon combinations; (3) said processed tissue in non-native form comprises solubilized or purified collagen from connective tissue, gelatin from mammals or fish or demineralized bone; (4) said composites comprise combinations of native tissues, processed tissues in native form and/or processed tissues in non-native form, such as pericardium with gelatin, bone with gelatin, purified collagen with gelatin or demineralized bone with solubilized or purified collagen; and (5) said complex composite comprises native tissue, processed tissue in native form, processed tissue in non-native form or a composite of native tissue, processed tissue in native form and/or processed tissue in non-native form with a biocompatible material such as a hydrogel, an alginate and/or chitosan. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans, glycosaminoglycans, growth factors, including any member of the transforming growth factor (TGF) superfamily and proteoglycans; (2) a deoxyribonucleic acid; (3) ribonucleic acid, such as a small interfering RNA or microRNA; (4) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) a ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the bioimplant is in the form of a suture, a sheet, an implantable valve, an implantable sponge or an implantable paste. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a bioimplant comprising a chemically sterilized biological tissue and at least one adjunct, wherein the adjunct is covalently conjugated to the biological tissue, comprising: (a) contacting a biological tissue with an adjunct to form a combination; and (b) contacting the combination with a chemical sterilizing agent to form the bioimplant. In some embodiments, the sterilizing agent is a carbodiimide, such as EDC, optionally in the presence of an alkanol, such as a $C_2$-$C_4$ alkanol, especially isopropanol. In some embodiments, the biological tissue comprises native tissue, processed tissue in native form, processed tissue in non-native form, a composite or a complex composite. In some embodiments: (1) said native tissue comprises bone, tendon, ligament, dermis, fascia, pericardium, said native tissue comprises bone, tendon, ligament, dermis, fascia, pericardium, and combinations thereof, including bone-connective tissue combinations, such as bone-tendon combinations and bone-ligament-bone combinations; (2) said processed tissue in native form comprises crosslinked tissue, decellularized crushed bone fragments, decellularized collagen or other decellularized and/or defatted bone, tendon, ligament, fascia or bone-connective tissue combinations, such as bone-ligament-bone or bone-tendon combinations; (3) said processed tissue in non-native form comprises solubilized or purified collagen from connective tissue, gelatin from mammals or fish or demineralized bone; (4) said composites comprise combinations of native tissues, processed tissues in native form and/or processed tissues in non-native form, such as pericardium with gelatin, bone with gelatin, purified collagen with gelatin or demineralized bone with solubilized or purified collagen; and (5) said complex composite comprises native tissue, processed tissue in native form, processed tissue in non-native form or a composite of native tissue, processed tissue in native form and/or processed tissue in non-native form with a biocompatible material such as a hydrogel, an alginate and/or chitosan. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (3) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the method includes shaping or forming the biological tissue into the form of a suture, a sheet, an implantable valve, an implantable sponge or an implantable paste. In some embodiments, the invention provides a bioimplant made by the process comprising contacting a biological tissue with an adjunct molecule in the presence of a sterilizing agent, as described herein. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a sterilized biological implant, comprising: (a) contacting a starting tissue with an adjunct to form an intermediate; (b) freezing the intermediate product of (a) to produce a frozen intermediate; (c) lyophilizing the frozen intermediate from (b) to produce a lyophilized intermediate; and (d) contacting the lyophilized intermediate with a sterilizing solution comprising a carbodiimide sterilizing agent to produce the biological implant. In some embodiments, the sterilizing agent is a carbodiimide, such as EDC, optionally in the presence of an alkanol, such as a $C_2$-$C_4$ alkanol, especially isopropanol. In some embodiments, the starting tissue is a native tissue, a processed tissue in native form or a composite tissue. In some embodiments, the starting tissue is: (1) a native tissue comprising bone, tendon, ligament, dermis, fascia, pericardium, and combinations thereof, including bone-connective tissue combinations, such as bone-tendon combinations and bone-ligament-bone combinations; (2) said processed tissue in native form comprises crosslinked tissue, decellularized crushed bone fragments, decellularized collagen or other decellularized and/or defatted bone, tendon, ligament, fascia or bone-connective tissue combinations, such as bone-ligament-bone or bone-tendon combinations; or (3) a composite comprising combinations of native tissues, processed tissues in native form and/or processed tissues in non-native form, such as pericardium with gelatin, bone with gelatin, purified collagen with gelatin or demineralized bone with solubilized or purified collagen. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β) (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β) (b) platelet derived growth factor (PDGF); (c) fibroblast growth factor (FGF); (d) insulin-like growth factors (IGF); (e) cartilage-derived growth factors (CDGF); (3) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the method includes shaping or forming the biological tissue into the form of a suture, a sheet, an implantable valve, an implantable sponge or an implantable paste. In some embodiments, the invention provides a bioimplant produced by the foregoing methods. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a sterilized biological implant, comprising: (a) preparing a composition comprising a starting tissue; (b) freezing the composition from (a) to form a frozen composition; (c) lyophilizing the frozen composition from (b) to form a lyophilized composition; and (d) contacting the lyophilized composition from (c) with a sterilizing solution comprising a sterilizing agent and an adjunct to produce the biological implant. In some embodiments, the sterilizing agent is a carbodiimide, such as EDC, optionally in the presence of an alkanol, such as a $C_2$-$C_4$ alkanol, especially isopropanol. In some embodiments, the starting tissue is a processed tissue in native form or a complex composite. In some embodiments, the starting tissue is: (1) a processed tissue in native form comprising crosslinked tissue, decellularized crushed bone fragments, decellularized collagen or other decellularized and/or defatted bone, tendon, ligament, fascia or bone-connective tissue combinations, such as bone-ligament-bone or bone-tendon combinations; or (2) complex composite comprising native tissue, processed tissue in native form, processed tissue in non-native form or a composite of native tissue, processed tissue in native form and/or processed tissue in non-native form with a biocompatible material such as a hydrogel, an alginate and/or chitosan. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β) (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β) (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (3) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the method further comprises shaping or forming the biological tissue into the form of a suture, a sheet, an implantable valve, an implantable sponge or an implantable paste. In some embodiments, the invention provides a biological implant produced by the process described herein. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a sterilized biological implant, comprising: (a) contacting a starting tissue with a crosslinking agent to at least partially crosslink the starting tissue to produce a crosslinked tissue; and (b) contacting the crosslinked tissue from (a) with a sterilizing solution comprising a sterilizing agent and an adjunct to produce the biological implant. In some embodiments, the sterilizing agent is a carbodiimide, such as EDC, optionally in the presence of an alkanol, such as a $C_2$-$C_4$ alkanol, especially isopropanol. In some embodiments, the starting tissue is a native tissue or a processed tissue in native form. In some embodiments, the starting tissue is: (1) a native tissue comprising bone, tendon, ligament, dermis, fascia, pericardium, or combinations thereof, including bone-connective tissue combinations, such as bone-tendon combinations and bone-ligament-bone combinations; or (2) a processed tissue in native form comprising crosslinked tissue, decellularized crushed bone fragments, decellularized collagen or other decellularized and/or defatted bone, tendon, ligament, fascia or bone-connective tissue combinations, such as bone-ligament-bone or bone-tendon combinations. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the process of the invention further comprises shaping or forming the biological tissue into the form of a suture, a sheet, an implantable valve, an implantable sponge or an implantable paste. In some embodiments, the invention provides a bioimplant produced by a process as described herein. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a sterilized biological implant, comprising: (a) contacting a starting tissue with a crosslinking agent and an adjunct to at least partially crosslink the starting tissue to produce a crosslinked tissue adjunct-conjugated tissue; and (b) contacting the crosslinked tissue from (a) with a sterilizing solution comprising a sterilizing agent to produce the biological implant. In some embodiments, the sterilizing agent is a carbodiimide, such as EDC, optionally in the presence of an alkanol, such as a $C_2$-$C_4$ alkanol, especially isopropanol. In some embodiments, the starting tissue is a processed tissue in non-native form. In some embodiments, the starting tissue is a processed tissue in non-native form comprising solubilized or purified collagen from connective tissue, gelatin from mammals or fish or demineralized bone. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (3) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the process of the invention comprises shaping or forming the biological tissue into the form of a suture, a sheet, an implantable valve, an implantable sponge or an implantable paste. In some embodiments, the invention further provides a bioimplant produced by the process described herein. In some embodiments, the adjunct retains at least some of its native activity after it has been conjugated to the biological tissue. In some embodiments, the adjunct is adapted to be released in vivo and the adjunct, once release in vivo possesses at least some of its native activity.

In some embodiments, the invention provides a process of making a sterilized biological implant, comprising: (a) contacting a starting tissue with a sterilizing solution comprising a sterilizing agent to produce a sterilized intermediate; (b)

contacting the sterilized intermediate from (a) with an adjunct and a conjugating agent to produce an implant; and (c) optionally subjecting the implant to another sterilization step; whereby a sterilized biological implant is produced. In some embodiments, the sterilizing agent is a carbodiimide, such as EDC, optionally in the presence of an alkanol, such as a $C_2$-$C_4$ alkanol, especially isopropanol. In some embodiments, the starting tissue is a processed tissue in non-native form. In some embodiments, the starting tissue is: (1) a native tissue, such as bone, tendon, ligament, dermis, fascia, pericardium, and combinations thereof, including bone-connective tissue combinations, such as bone-tendon combinations and bone-ligament-bone combinations; (2) a processed tissue in non-native form, such as solubilized or purified collagen from connective tissue, gelatin from mammals or fish or demineralized bone; or (3) combinations of native tissues, processed tissues in native form and/or processed tissues in non-native form, such as pericardium with gelatin, bone with gelatin, purified collagen with gelatin or demineralized bone with solubilized or purified collagen. In some embodiments, the adjunct is a protein, a small peptide, a ribonucleic acid, a deoxyribonucleic acid, a polysaccharide, glycosaminoglycan (GAG) or an antibiotic. In some embodiments, the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-$\beta$ (TGF-$\beta$); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, $\beta$-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the adjunct is (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-$\beta$ (TGF-$\beta$); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) an antibiotic, such as one or more aminoglycosides, amphenicols, ansamycins, $\beta$-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In some embodiments, the biological tissue comprises collagen, purified collagen or solubilized collagen. In some embodiments, the process of the invention comprises shaping or forming the biological tissue into the form of a suture, a sheet, an implantable valve, an implantable sponge or an implantable paste. In some embodiments, the invention provides a bioimplant produced by the process of the invention. In some embodiments, the adjunct retains at least some of its native activity after it has been conjugated to the biological tissue. In some embodiments, the adjunct is adapted to be released in vivo and the adjunct, once release in vivo possesses at least some of its native activity.

Other advantages of the present invention will become apparent to the person of skill in the art upon consideration of the following description and claims.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of embodiments of the present invention will be obtained by reference to the following detailed description that sets forth illustrative embodiments, in which the principles of the invention are utilized, and the accompanying drawings of which:

FIGS. 5A-5C are light microscopic pictures of Control (FIG. 5A), partial GAG-modified (FIG. 5B) and complete GAG-modified (FIG. 5C) pericardium. The tissue sections were stained with PAS-Alcian Blue; GAGs stain blue and collagen stains pink. These figures show the successful attachment of GAG to crosslinked and sterilized pericardial tissue by methods according to the present invention.

FIGS. 6A and 6B are low- and high-magnification images of Type 1 collagen sponge in which GAG has been attached to the collagen sponge during sterilization. As can be seen in FIGS. 6A and 6B, attachment of GAG to collagen sponge during sterilization leads to diffuse attachment of the GAG to the collagen sponge.

FIG. 7A is a picture of a histological section of cancellous bone having GAG attached thereto.

FIG. 7B is a picture of a histological section of Type I collagen sponge having GAG attached thereto during cross-linking by a method according to the present invention.

FIGS. 8A and 8B are pictures of histological sections of collagen sponge having hyaluronic acid attached thereto by a method according to the present invention.

FIG. 8C is a picture of a histological section of pericardium having hyaluronic acid attached thereto by a method according to the present invention.

FIG. 8D is a graph of results of a reverse ELISA assay for IGF-1 bound to collagen sponge by a method according to the present invention. Decreased ELISA signal in the IGF FX/STER assay versus the control assay indicates that anti-IGF antibody has bound to IGF in the IGF FX/STER sample, thus yielding a depressed ELISA signal in the anti-IGF antibody solution that has contacted the IGF FX/STER sample as compared to the signal in the anti-IGF antibody solution that has contacted the control sample.

FIG. 9 is a graph of results from a cell-viability assay. Control and chondroitin-sulfate attached collagen sponges were seeded with primary chondrocytes and incubated. Human chondrocyte-seeded collagen sponge was evaluated on day 7, while bovine chondrocyte-seeded collagen sponge was evaluated on day 14. The results of a cell viability assay (MTT) demonstrate the increased cell viability in chondroitin sulfate-attached collagen sponge (red) versus control (untreated) collagen sponge (blue).

FIGS. 10A, 10B and 10C are pictures of MTT assays of histological sections of chondrocyte-seeded GAG-attached collagen sponge according to the present invention. FIGS. 10A and 10B are low- and high-magnification images of MTT-treated GAG-attached collagen sponge seeded with chondrocytes. Viable cells are stained purple and the presence of newly synthesized matrix is seen around the cells as a thin fibrinous layer. FIG. 10C is a high-magnification image of the chondrocyte-seeded GAG-attached collagen sponge showing the appearance of newly synthesized matrix.

FIGS. 11A and 11B are histological sections of GAG-attached cellulose sponge. Selected samples of GAG-attached collagen sponge were implanted subcutaneously into rats. Explants were retrieved 4 weeks later and sections were stained with PAS-Alcian Blue (FIG. 11A) or hematoxylin and eosin (H&E; FIG. 11B). As can be seen in FIG. 11A, GAG remains attached to the cellulose matrix even after 4 weeks, as evidenced by the blue staining. The absence of overt and active inflammation and the appearance of new matrix and blood vessels between the collagen strands of the tissues (FIG. 11B) indicate a biocompatible response from the host.

DETAILED DESCRIPTION OF THE INVENTION

Figure 1:
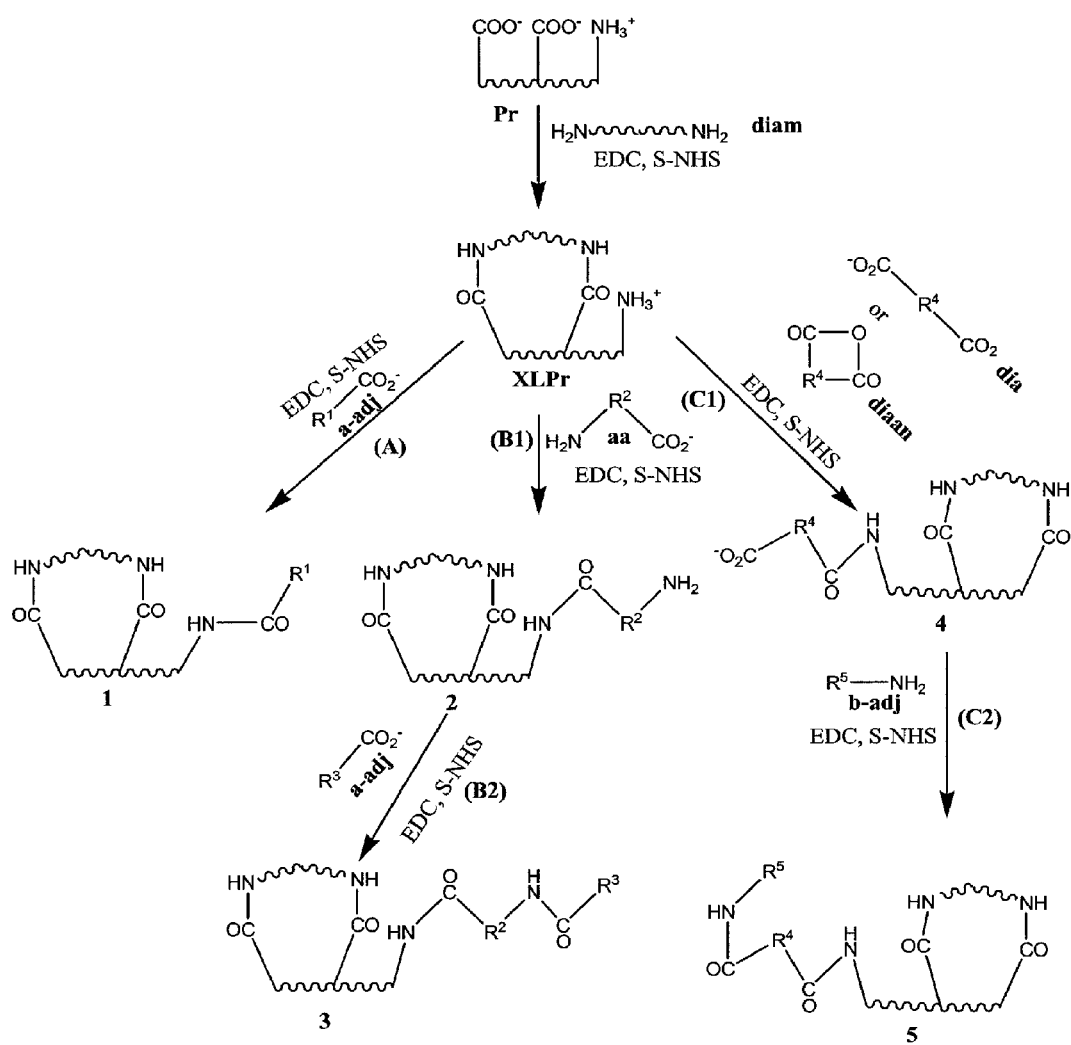
FIG. 1 shows three different chemical reaction schemes for preparing a bioimplant of the present invention.

The present invention provides bioimplants and processes of making those bioimplants. Generally speaking, the bioimplants comprise biological tissues that are sterilized, preferably chemically sterilized, and have adjunct molecules covalently attached (conjugated) thereto. Such bioimplants have notable advantages over prior art biological tissues, such as improved wound healing, tissue remodeling, tissue growth and tissue regrowth. Additionally, because the adjuncts are conjugated to the biological tissues, in some embodiments they are released at a rate that is generally less than the rate of diffusion of the adjunct from similar biological tissues wherein the adjuncts are merely infused into the biological tissues. This is especially advantageous for growth factors and other adjuncts that have activity at very low concentrations, but that are advantageously delivered over a long period of time. This is also advantageous for small molecules, which being of lower molecular weight, diffuse relatively rapidly out of tissues when they are merely infused therein. Covalent conjugation of the small molecules to the biological tissue permits a slower, more regulated release of the adjunct, thereby providing an effective local activity of the adjunct over a longer period of time. In some embodiments, the adjunct molecules retain native activity when conjugated to the biological tissue; and in some embodiments the adjunct molecules regain native activity when released from the biological tissue. Other advantages of the bioimplant of the present invention will become apparent to the person of skill in the are upon consideration of the disclosure herein.

As used herein, the term "bioimplant" refers to a device comprising a biological tissue that has been subjected to one or more process steps to render it amenable to implantation. In general, the bioimplant is a chemically sterilized bioimplant having conjugated thereto at least one adjunct. In particular embodiments, the bioimplant is chemically sterilized with a water soluble carbodiimide, such as 1-ethyl-3-(3-dimethylaminopropyl)carbodiimide hydrochloride (EDC). In some embodiments, the biological tissue is crosslinked with a suitable crosslinking agent, such as a diamine or other bifunctional crosslinking reagent, optionally in the presence of a coupling agent and/or a coupling enhancer. Carbodiimide-mediated crosslinking is described in detail in U.S. Pat. No. 5,733,339 and U.S. Patent Publication No. US2004253291, the entirety of each of which is incorporated herein by reference. In some particular embodiments, the invention specifically excludes bioimplants comprising biological tissue that has been treated with glutaraldehyde, especially glutaraldehyde solution or vapor.

The bioimplants of the present invention comprise a biological tissue that is sterilized, especially chemically sterilized. In particular, the present invention provides a bioimplant that comprises a biological tissue that has been sterilized with a chemical agent capable of reducing the population of bacteria and/or spores in the biological tissue by at least 3 logs, especially at least about 4 logs, more especially at least 5 logs, and particularly at least about 6 logs. Exemplary sterilizing agents include a carbodiimide such as 1-ethyl-3-(3-dimethyl aminopropyl)carbodiimide hydrochloride (EDC). The use of EDC as a sterilizing agent is described in detail e.g. in U.S. Pat. No. 5,911,951, the entirety of which is incorporated herein by reference. In some particular embodiments, the invention specifically excludes those bioimplants sterilized with γ-radiation. In other particular embodiments, the invention excludes tissues sterilized solely with γ-radiation.

The bioimplants of the present invention have covalently bonded to them at least one "adjunct molecule," also referred to herein simply as an "adjunct." The adjunct molecule is a non-endogenous molecule that promotes tissue healing, remodeling, growth or regrowth in the recipient body. The adjunct molecule exerts this tissue healing, remodeling, growth or regrowth activity in the conjugated state (that is while bound to the bioimplant) or upon release into the immediate environment of the bioimplant. The adjunct molecule is non-endogenous in the sense that it is outside the body of the bioimplant recipient when it is conjugated to, and becomes part of, the bioimplant. Thus adjunct molecules specifically exclude growth factors and other molecules that are within the body of the bioimplant recipient at the time of implantation and become covalently bonded to the bioimplant only incidentally and only during or after implantation of the bioimplant. However, adjunct molecules specifically include molecules from within the body of the intended recipient that are isolated, purified or otherwise treated to enhance their concentration, purity, activity or a combination thereof, before being conjugated to the biological tissue outside the recipient's body.

As used herein, the terms "conjugated" and "attached" and their various linguistic forms, mean that the adjunct is covalently attached to the biological tissue, either directly or indirectly. A direct covalent attachment between the adjunct and the biological tissue is a covalent bond formed between a side chain of the biological tissue and a side chain of the adjunct. An indirect covalent attachment formed through an intermediate "linker." The linker is a moiety, which is the residue of a multifunctional (e.g. a bifunctional) molecule capable of forming covalent bonds with side chains on both the biological tissue and the adjunct. Thus, an indirect covalent bond between the adjunct and the biological tissue is a covalent linkage comprising a first covalent bond between a side chain of the adjunct and a reactive group on a linking moiety and a second covalent bond between the linking moiety and a side chain of the biological tissue. Suitable covalent bonds are formed as amides, esters, ethers, ureas, carbamates, carbonates, anhydrides and other covalent bonds. Especially suitable covalent bonds are amides. An amide may be formed directly between an acid group on an adjunct and an amine on a protein or glycosamine of the biological tissue or between an amine on an adjunct and an acid group on a protein in the biological tissue. An indirect covalent attachment comprising an amide bond may be formed, for example, through a diacid linker, an amino acid linker, or a diamine linker using a conjugation agent.

In some embodiments, adjuncts are proteins, small peptides, ribonucleic acid (RNA), deoxyribonucleic acid (DNA), polysaccharide, proteoglycans, glycosaminoglycan (GAGs), such as hyaluronan, chondroitin sulfate, keratin sulfate, dermatan sulfate, heparin or heparan sulfate, or antibiotics, as described in more detail below. The source of such adjuncts can be biological tissues (especially in the case of proteins, small peptides, RNA and DNA), cell cultures (especially in the cases of recombinant proteins, small peptides, RNA, DNA and antibiotics), or synthetic sources (especially in the case of certain antibiotics and small RNA, DNA and peptides). The adjuncts promote tissue healing, remodeling, growth or regrowth while bound to the bioimplant (conjugated state), after release from the bioimplant or both.

In some embodiments of the invention, the bioimplant comprises an adjunct that is a protein, especially a growth factor or a proteoglycan. Suitable growth factors that may be mentioned include all members of the transforming growth factor (TGF) superfamily, including BMP-2, BMP-4, BMP-7 and BMP-13, etc. Other suitable proteins include the proteoglycans, including proteoglycans having associated glycosaminoglycans (GAGs), such as hyaluronan, chondroitin sulfate, keratin sulfate, dermatan sulfate, heparin or heparan sulfate, In some embodiments, the adjunct molecule is a deoxyribonucleic acid (DNA), a ribonucleic acid (RNA) or a mimetic of DNA or RNA. Deoxyribonucleic acids include genes and gene fragments as well as antisense molecules capable of binding to and silencing and/or regulating one or more genes, such as a bacterial or viral gene. Ribonucleic acids include small interfering RNA (siRNA) and microRNA, as well as structurally modified versions of siRNA and microRNA, which are capable of silencing a gene, such as a bacterial or viral gene. RNA and DNA also include one or more plasmids capable of invading a bacterium and expressing a gene product that is bacteriostatic or that is lethal to the bacterium or a virus. DNA and RNA also include plasmids capable of expressing siRNA or microRNA that silence and/or regulate one or more genes in a bacterium or in a virus, a co-infecting bacterium or other pathogenic microbe. In particular embodiments, the DNA and RNA adjuncts become active in vivo after the conjugations between the DNA or RNA and the bioimplant are broken, e.g. by hydrolysis of one or more covalent bonds between the DNA or RNA and the biological tissue. In some embodiments, the DNA or RNA is active while conjugated to the biological tissue.

In some embodiments, the adjunct molecule is an antibiotic. Because the adjuncts are covalently attached to the biological tissues, they are released into the environment only upon cleavage of the covalent bond, e.g. by hydrolysis. This provides for release of the antibiotic at a rate that is in some cases slower than the diffusive rate of release of a like quantity of free antibiotic or antibiotic infused in a tissue. Suitable antibiotic adjuncts include aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. The antibiotics exert their tissue healing, remodeling, growth or regrowth activity by interfering with bacterial growth within the vicinity of the bioimplant after it has been implanted in the recipient body. In particular, the antibiotics exert their tissue healing, remodeling, growth or regrowth activity by exerting bacteriocidal or bacteriostatic effects on bacteria in the vicinity of the bioimplant. Some such antibiotics are bacteriocidal or bacteriostatic while they are conjugated to the bioimplant. Other such antibiotics are activated to a bacteriocidal or bacteriostatic state after the conjugations between the antibiotics and the tissue are broken, e.g. by hydrolyzing one or more amide, ester, urea or anhydride bonds between the antibiotics and the bioimplant. Some advantages of using antibiotic conjugated biological tissues as bioimplants include the following: the local concentration of antibiotic can be high, whereas systemic concentration remains low, thus localizing the antibacterial effect of the antibiotic and reducing systemic toxicity; slow release of antibiotic from the biological tissue conserves antibacterial activity over a long course of time; reduced deleterious effect on non-pathogenic commensal bacteria, especially in the gut; and potentially reduced induction of antibiotic-resistance in bacteria.

Biological Tissues

The present invention provides bioimplants comprising sterilized biological tissues that have conjugated to them one or more adjunct molecules. Suitable biological tissues are those tissues amenable to implantation in a host body to repair or replace injured or removed host tissue or to promote healing, remodeling, growth or regrowth of host tissue. In some embodiments, the biological tissue is native tissue, a processed tissue in native form, a processed tissue in non-native form, a composite or a complex composite. The tissues may be autogenic, allogenic or xenogenic in origin. The term "native tissue" means that the tissue from which the implant is prepared ("starting tissue") is not processed prior to conjugating the adjunct to it. In particular, "native tissue" is not defatted, decellularized or crosslinked prior to conjugating the adjunct to it. Suitable native tissues include bone, tendon, ligament, dermis, fascia, pericardium and combinations thereof, such as bone-connective tissue combinations, including bone-tendon combinations and bone-ligament-bone combinations. The term "processed tissue in native form" means that the starting tissue is subjected to one or more processing steps, such as decellularization, defatting or crosslinking prior to conjugation of the adjunct to the tissue, but otherwise remains in substantially the same form as in the native tissue. Suitable processed tissues in native form include crosslinked tissue, decellularized crushed bone fragments, decellularized collagen or other decellularized and/or defatted bone, tendon, ligament, fascia and combinations thereof, such as bone-connective tissue combinations, e.g. bone-tendon or bone-ligament-bone combinations. The term "processed tissue in non-native form" means tissue that has been processed in such a way that the tissue is no longer in its native form, e.g. through solubilization, reconstitution or some other process that changes its form from its native form. Suitable processed tissues in non-native form include solubilized or purified collagen from connective tissue, gelatin from mammals or fish or demineralized bone. A "composite" is a combination of two or more members of the group of native tissues, processed tissues in native form and processed tissues in non-native form. Suitable composites include combinations of native tissues, processed tissues in native form and/or processed tissues in non-native form, such as pericardium, with gelatin, bone with gelatin, purified collagen with gelatin or demineralized bone with solubilized or purified collagen. A "complex composite" is a combination of one or more native tissues, processed tissues in native form, processed tissues in non-native form, and composites with a biocompatible material, such as a synthetic or non-mammalian (e.g. crustacean- or plant-derived) biocompatible material. Suitable complex composite comprises native tissue, processed tissue in native form, processed tissue in non-native form or a composite of native tissue, processed tissue in native form and/or processed tissue in non-native form with a biocompatible material such as a hydrogel, an alginate and/or chitosan.

Tissue may be decellularized by an art-recognized method, such as treatment with trypsin or sodium dodecylsulfate (SDS). Rieder et al., "Decellularization protocols of porcine heart valves differ importantly in efficiency of cell removal and susceptibility of the matrix to recellularization with human vascular cells," J. Thorac. Cardiovasc. Surg., 127, 399-405 (2004); Kasimir et al., "Comparison of different decellularization procedures of porcine heart valves," Int. J. Artif. Organs, 26(5), 421-427 (2003). In some embodiments, SDS treatment may leave some cells on the scaffold. Reider et al., 2003. In some embodiments, such residual cells or cell fragments may not be deleterious, as crosslinking and/or sterilization would be expected to neutralize such residual structures. In any case, should treatment with trypsin and/or SDS fail to produce a suitable starting material, decellularization may be effected with another known decellularization method, such as treatment with a combination of tert-octylphenylpolyoxyethylene and sodium deoxycholate (Rieder et al., 2003) or a non-ionic detergent, such as Triton-X 100 (Kasimir, 2003). The person skilled in the art will recognize that other decellularization methods may be employed and are thus within the scope of the present invention.

Bone tissue, such as solid bone and bone fragments, may be demineralized by an art-recognized method. Such demineralization may be in conjunction with, or independent of, decellularization as described above. Such demineralization may be partial or complete. Partial demineralization is often used to modify cortical bone grafts to enhance their osteoinductive properties. Danilchenko et al., "X-ray diffraction studies of bone apatite under acid demineralization," Cryst. Res. Technol., 39(1), 71-77 (2004). Bone tissue may also be demineralized by treatment with a weak acid, such as acetic acid. Demineralization removes mineral content (such as calcium carbonate) of the bone, leaving osteoinductive agents in tact in the demineralized bone matrix. Laurencin, "Bone Graft Substitute Materials," eMedicine (available online only), http://www.emedicine.com/orthop/topic611.htm, updated Mar. 15, 2005. Demineralized bone matrix has been shown to induce new bone formation in vivo. Salih et al., "Natural variation in the extent of phosphorylation of bone phosphoproteins as a function of in vivo new bone formation induced by demineralized bone matrix in soft tissue and bony environments," Biochemical Journal, 364, 465-474 (2002), accessed at http://www.biochemj.org/364/0465/bj3640465.htm. Thus, bone tissue, such as whole bone or bone fragments may be demineralized in the presence of a weak acid solution, such as 0.05 to 0.5 M HCl or other mineral acid, or in the presence of a weak acid such as acetic acid. The resulting partially demineralized bone or fully demineralized bone matrix (DBM) may then be conjugated with an adjunct molecule and sterilized and optionally crosslinked as described in more detail below.

Bioimplants

The invention provides a bioimplant comprising a chemically sterilized biological tissue and at least one adjunct, wherein the adjunct is covalently conjugated to the biological tissue. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue used in the bioimplants may comprise native tissue, processed tissue in native form, processed tissue in non-native form, a composite or a complex composite. In preferred embodiments, the biological tissue is a native tissue, a processed tissue in non-native form or a composite. In particular embodiments, the biological tissue is a native tissue, which comprises bone, tendon, ligament, dermis, fascia, pericardium, or combinations thereof, including bone-connective tissue combinations, such as bone-tendon combinations and bone-ligament-bone combinations. In other embodiments, the biological tissue is a processed tissue in native form, which comprises crosslinked tissue, decellularized crushed bone fragments, decellularized collagen or other decellularized and/or defatted bone, tendon, ligament, fascia and bone-connective tissue combinations, such as bone-ligament-bone or bone-tendon combinations. In other embodiments, the biological tissue is processed tissue in non-native form, which comprises solubilized or purified collagen from connective tissue, gelatin from mammals or fish or demineralized bone. In still further embodiments, said tissue comprises a composite material, which comprise combinations of native tissues, processed tissues in native form and/or processed tissues in non-native form, such as pericardium with gelatin, bone with gelatin, purified collagen with gelatin or demineralized bone, with solubilized or purified collagen. In still further embodiments, the biological tissue is a complex composite tissue, which comprises native tissue, processed tissue in native form, processed tissue in non-native form or a composite of native tissue, processed tissue in native form and/or processed tissue in non-native form with a biocompatible material such as a hydrogel, an alginate and/or Chitosan. In preferred embodiments, the invention provides a bioimplant, wherein the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG), glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In particularly preferred embodiments, the bioimplant is in the form of a suture, a sheet, an implantable valve, an implantable sponge or an implantable paste.

In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. As used herein, the term "at least some" means at least about 5%. Thus, in embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment. As used herein the term "native activity" means that activity possessed by the adjunct prior to being conjugated to the biological tissue. In general, native activity is tested under in vivo conditions or under in vitro conditions designed to simulate in vivo conditions.

General Process

In some embodiments, the invention provides a process of making the bioimplant, comprising: (a) contacting a biological tissue with an adjunct to form a combination; and (b) contacting the combination with a chemical sterilizing agent to form the bioimplant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue may comprise native tissue, processed tissue in native form, processed tissue in non-native form, a composite or a complex composite. In particular embodiments, the biological tissue is a native tissue, which comprises bone, tendon, ligament, dermis, fascia, pericardium, or combinations thereof, including bone-connective tissue combinations, such as bone-tendon combinations and bone-ligament-bone combinations. In other embodiments, the biological tissue is a processed tissue in native form, which comprises crosslinked tissue, decellularized crushed bone fragments, decellularized collagen or other decellularized and/or defatted bone, tendon, ligament, fascia and bone-connective tissue combinations, such as bone-ligament-bone or bone-tendon combinations. In other embodiments, the biological tissue is processed tissue in non-native form, which comprises solubilized or purified collagen from connective tissue, gelatin from mammals or fish or demineralized bone. In still further embodiments, said tissue comprises a composite material, which comprise combinations of native tissues, processed tissues in native form and/or processed tissues in non-native form, such as pericardium with gelatin, bone with gelatin, purified collagen with gelatin or demineralized bone, with solubilized or purified collagen. In still further embodiments, the biological tissue is a complex composite tissue, which comprises native tissue, processed tissue in native form, processed tissue in non-native form or a composite of native tissue, processed tissue in native form and/or processed tissue in non-native form with a biocompatible material such as a hydrogel, an alginate and/or Chitosan. In preferred embodiments, the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent.

In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. In some embodiments of this process, the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment.

Lyophilization—Variant 1: Adding Adjunct Prior to Freezing

In some embodiments, the invention provides a process of making a sterilized biological implant, comprising: (a) contacting a starting tissue with an adjunct to form an intermediate; (b) freezing the intermediate product of (a) to produce a frozen intermediate; (c) lyophilizing the frozen intermediate from (b) to produce a lyophilized intermediate; and (d) contacting the lyophilized intermediate with a sterilizing solution comprising a carbodiimide sterilizing agent to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue may comprise native tissue, processed tissue in native form, processed tissue in non-native form, a composite or a complex composite. In preferred embodiments, the biological tissue is a native tissue or a composite. In particular embodiments, the biological tissue is a native tissue, which comprises bone, tendon, ligament, dermis, fascia, pericardium, or combinations thereof, including bone-connective tissue combinations, such as bone-tendon combinations and bone-ligament-bone combinations. In other embodiments, said tissue comprises a composite material, which comprise combinations of native tissues, processed tissues in native form and/or processed tissues in non-native form, such as pericardium with gelatin, bone with gelatin, purified collagen with gelatin or demineralized bone, with solubilized or purified collagen. In some preferred embodiments, the invention provides a bioimplant, wherein the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol.

In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent.

In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. In some embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment.

Lyophilization—Variant 2: Adding Adjunct with Sterilizing Agent

In some embodiments, the invention provides a process of making a sterilized biological implant, comprising: (a) preparing a composition comprising a starting tissue; (b) freezing the composition from (a) to form a frozen composition; (c) lyophilizing the frozen composition from (b) to form a lyophilized composition; and (d) contacting the lyophilized composition from (c) with a sterilizing solution comprising a sterilizing agent and an adjunct to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue may comprise native tissue, processed tissue in native form, processed tissue in non-native form, a composite or a complex composite. In preferred embodiments, the biological tissue is a processed tissue in native form or a complex composite. In some embodiments, the biological tissue is a processed tissue in native form, which comprises crosslinked tissue, decellularized crushed bone fragments, decellularized collagen or other decellularized and/or defatted bone, tendon, ligament, fascia and bone-connective tissue combinations, such as bone-ligament-bone or bone-tendon combinations. In other embodiments, the biological tissue is a complex composite tissue, which comprises native tissue, processed tissue in native form, processed tissue in non-native form or a composite of native tissue, processed tissue in native form and/or processed tissue in non-native form with a biocompatible material such as a hydrogel, an alginate and/or Chitosan. In preferred embodiments, the invention provides a bioimplant, wherein the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, tauroldine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, tauroldine and xibernol. In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent. In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. In some embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment.

Process Using Crosslinked Biological Tissue

In some embodiments, the invention provides a process of making a sterilized biological implant, comprising: (a) contacting a starting tissue with a crosslinking agent to at least partially crosslink the starting tissue to produce a crosslinked tissue; and (b) contacting the crosslinked tissue from (a) with a sterilizing solution comprising a sterilizing agent and an adjunct to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue may comprise native tissue, processed tissue in native form, processed tissue in non-native form, a composite or a complex composite. In preferred embodiments, the biological tissue comprises native tissue or processed tissue in native form. In particular embodiments, the biological tissue is a native tissue, which comprises bone, tendon, ligament, dermis, fascia, pericardium, or combinations thereof, including bone-connective tissue combinations, such as bone-tendon combinations and bone-ligament-bone combinations. In other embodiments, the biological tissue is a processed tissue in native form, which comprises crosslinked tissue, decellularized crushed bone fragments, decellularized collagen or other decellularized and/or defatted bone, tendon, ligament, fascia and bone-connective tissue combinations, such as bone-ligament-bone or bone-tendon combinations.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent.

In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. In some embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment.

Process—Adding Crosslinking Agent and Adjunct Simultaneously

In some embodiments, the invention provides a process of making a sterilized biological implant, comprising: (a) contacting a starting tissue with a crosslinking agent and an adjunct to at least partially crosslink the starting tissue to produce a crosslinked tissue adjunct-conjugated tissue; and (b) contacting the crosslinked tissue from (a) with a sterilizing solution comprising a sterilizing agent to produce the biological implant. In some embodiments, the bioimplant is chemically sterilized with a water soluble carbodiimide, such as EDC. In some embodiments, the sterilization is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS).

The biological tissue may comprise native tissue, processed tissue in native form, processed tissue in non-native form, a composite or a complex composite. In some preferred embodiments, the biological tissue is a processed tissue in non-native form. In some preferred embodiments, the biological tissue is processed tissue in non-native form, which comprises solubilized or purified collagen from connective tissue, gelatin from mammals or fish or demineralized bone. In preferred embodiments, the invention provides a bioimplant, wherein the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent.

In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. In some embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment.

Process—Sterilization Prior to Addition of Adjuncts

In other embodiments, the invention provides a process of making a sterilized biological implant, comprising: (a) contacting a starting tissue with a sterilizing solution comprising a sterilizing agent to produce a sterilized intermediate and; (b) contacting the sterilized intermediate from (a) with an adjunct to produce the biological implant; and (c) optionally subjecting the implant to another sterilization step. The process produces a sterilized and adjunct-conjugated biological implant. In some embodiments, the first sterilization step (a) is carried out with a sterilization solution comprising a water-soluble carbodiimide, such as EDC. In some embodiments, the sterilization step (a) is carried out in the presence of a penetration enhancer, especially a water-soluble penetration enhancer having from 1 to about 6 carbon atoms and at least one polar group. In preferred embodiments, the penetration enhancer is an alcohol, such as a $C_1$-$C_6$ alkanol, especially a $C_2$-$C_4$ alkanol, and most particularly isopropanol. Other alcohols that may be mentioned in this regard include methanol, ethanol, n-propanol, n-butanol, i-butanol, t-butanol, and s-butanol, as well as n-pentanol, n-hexanol, cyclopropanol, cyclobutanol, cyclopentanol and cyclohexanol. In some embodiments, the chemically sterilized biological tissue is also crosslinked with a carbodiimide, optionally in the presence of a divalent crosslinking agent and/or a coupling enhancer, such as N-hydroxysuccinimide (NHS) or N-hydroxy-2-sulfosuccinimide (Sulfo-NHS). In some embodiments, the optional second sterilization (c) step is carried out in the same manner as the sterilization step (a); however in some embodiments the second sterilization is carried out in another manner, e.g. by γ-irradiation or gas sterilization. In some preferred embodiments, the second sterilization is carried out in the presence of a carbodiimide, especially a water soluble carbodiimide such as EDC, as described herein.

The biological tissue may comprise native tissue, processed tissue in native form, processed tissue in non-native form, a composite or a complex composite. In some preferred embodiments, the biological tissue comprises native tissue, processed tissue in non-native form or a composite. In particular embodiments, the biological tissue is a native tissue, which comprises bone, tendon, ligament, dermis, fascia, pericardium, or combinations thereof, including bone-connective tissue combinations, such as bone-tendon combinations and bone-ligament-bone combinations. In other embodiments, the biological tissue is processed tissue in non-native form, which comprises solubilized or purified collagen from connective tissue, gelatin from mammals or fish or demineralized bone. In still further embodiments, said tissue comprises a composite material, which comprise combinations of native tissues, processed tissues in native form and/or processed tissues in non-native form, such as pericardium with gelatin, bone with gelatin, purified collagen with gelatin or demineralized bone, with solubilized or purified collagen. In preferred embodiments, the invention provides a bioimplant, wherein the biological tissue comprises collagen, purified collagen or solubilized collagen.

In some embodiments, the adjunct is a protein, a small peptide, a ribonucleic acid, a deoxyribonucleic acid, a polysaccharide, glycosaminoglycan (GAG) or an antibiotic. In particular embodiments, the adjunct comprises: (1) one or more proteoglycans, glycosaminoglycans, growth factors, including any member of the transforming growth factor (TGF) superfamily and proteoglycans; (3) a deoxyribonucleic acid; (4) ribonucleic acid, such as a small interfering RNA or microRNA; (3) an antibiotic selected from aminoglycosides, the amphenicols, the ansamycins, the β-lactams, the lincosamides, the macrolides, the polypeptide antibiotics, the tetracyclines, cycloserine, mupirocin, tuberin, 2,4-diaminopyrimidines, the nitrofurans, the quinolones, the sulfonamides, the sulfones, clofoctol, hexedine, methenamine, nitroxoline, taurolidine and xibernol. In particular embodiments, the invention provides a bioimplant, wherein the adjunct comprises: (1) one or more proteoglycans or glycosaminoglycans, (2) one or more proteins, such as: (a) any member of the Transforming Growth Factor (TGF) superfamily, such as BMP-2, BMP-4 and BMP-7, transforming growth factor-β (TGF-β); (b) platelet derived growth factor (PDGF); (c) fibroblast growth factor (FGF); (d) insulin-like growth factors (IGF); (e) cartilage-derived growth factors (CDGF); (3) a deoxyribonucleic acid selected from genes, gene fragments and antisense DNA; (4) ribonucleic acid such as a small interfering RNA (siRNA) or a microRNA; or (5) an antibiotic, such as one or more aminoglycosides, amphenicols, ansamycins, β-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine and xibernol. In particularly preferred embodiments, the bioimplant is in the form of a suture, a sheet, an implantable valve, an implantable sponge or an implantable paste. In some embodiments, the process further comprises comprising shaping or forming the biological tissue into the form of a suture, a sheet, an implantable valve, an implantable sponge or an implantable paste. Moreover, the invention comprises a bioimplant made by the process comprising contacting a biological tissue with an adjunct molecule in the presence of a sterilizing agent. In preferred embodiments of the invention, the adjunct retains at least some of its native activity when conjugated to the biological tissue. In other preferred embodiments, the adjunct is released in vivo or under in vitro conditions designed to imitate in vivo conditions. In such preferred embodiments, the released adjunct has at least some native activity. As used herein, the term "at least some" means at least about 5%. Thus, in embodiments of the invention the conjugated adjunct has at least 5%, at least 10%, at least 15%, at least 20%, at least 25%, at least 30%, at least 50%, at least 60%, at least 70%, at least 80%, in particular about 5 to about 100%, about 10 to about 95%, about 15 to about 90%, or about 20 to about 80% of its native activity, either when bound to the biological tissue or when released from the biological tissue into the surrounding tissue in vivo or into an in vitro environment designed to simulate the in vivo environment. As used herein the term "native activity" means that activity possessed by the adjunct prior to being conjugated to the biological tissue. In general, native activity is tested under in vivo conditions or under in vitro conditions designed to simulate in vivo conditions.

Adjunct Molecules

The present invention provides a bioimplant comprising a sterilized biological tissue having at least one adjunct molecule conjugated thereto, e.g. through a side chain on a protein of the biological tissue. The adjunct molecule promotes healing, remodeling, growth and/or regrowth of biological tissue. Suitable adjunct molecules include: proteins, small peptides, nucleic acids (such as ribonucleic acids, deoxyribonucleic acids and their derivatives and mimetics) and antibiotics. In some embodiments, the adjunct protein is a growth factor or a proteoglycan. In particular embodiments, the protein is a growth factor such as transforming growth factor beta (TGF-β), platelet derived growth factor (PDGF), insulin-like growth factors (IGFs), cartilage derived growth factors (CDGF), fibroblast growth factor (FGF) and bone growth factors (BGFs). In specific embodiments, the bioimplant of the invention has one, two, three or more growth factors selected from TGF-β, PDGF, IGFs, CDGF, FGF and BGFs, covalently bonded to its surface. In some embodiments, the invention provides a bioimplant having one, two or more bone growth factors (BMPs) conjugate to the tissue. In some embodiments, the growth factors retain activity in the conjugated state and/or regain activity upon cleavage from the biological tissue. In some embodiments, the invention provides for controlled release of adjunct molecules, such as chondrogenic adjuncts (e.g. GAGs or growth factors). In some embodiments, the invention provides for controlled release of adjunct molecules, such as chondrogenic adjuncts, without substantial loss of adjunct activity due to sterilization.

In further embodiments, the invention provides a bioimplant having at least one glycosaminoglycan (GAG), small peptide, gene or gene fragment conjugated to the tissue. In some embodiments, the GAG retains activity in the conjugated state and/or regains activity upon cleavage from the biological tissue.

In still further embodiments, the invention provides a bioimplant having at least one antibiotic conjugated to the tissue. In some embodiments, the bioimplant has at least one antibiotic selected from aminoglycosides, the amphenicols, the ansamycins, the β-lactams, the lincosamides, the macrolides, the polypeptide antibiotics, the tetracyclines, cycloserine, mupirocin, tuberin and the synthetic antibacterial compounds such as 2,4-diaminopyrimidines, the nitrofurans, the quinolones, the sulfonamides, the sulfones, clofoctol, hexedine, methenamine, nitroxoline, taurolidine and xibernol. In some embodiments, the bioimplant has covalently bonded to the tissue, either alone or along with a β-lactam antibiotic, a β-lactamase inhibitor such as clavulanic acid. In some embodiments, the antibiotics retain activity in the conjugated state and/or regain activity upon cleavage from the biological tissue.

Bone Growth Factors (BGFs)

Various bone growth factors have been identified, including bone morphogenic (or morphogenetic) growth factors (BMPs).

Thus, in some embodiments, invention provides sterilized tissue having at least one type of bone growth factor (BGF) conjugated to the tissue. In some embodiments, the tissue is internally crosslinked as well as being conjugated to the BGF. In some embodiments, the invention provides a method of making a chemically sterilized bioimplant having a BGF covalently linked to biological tissue. In some embodiments, the BGF is conjugated to the biological tissue prior to sterilization; in other embodiments the BGF is conjugated to the biological tissue after sterilization; in still further embodiments conjugation and sterilization occur in the same process step. In some preferred embodiments, the BGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the BGF and biological tissue are combined, frozen, lyophilized and then sterilized. In some preferred embodiments, the BGF retains biological activity while conjugated to the biological tissue and/or after placement within a host, regains biological activity after being released from the biological tissue.

Bone Morphogenic Growth Factors (BMPs)

The bone morphogenic proteins comprise a superfamily of related proteins that stimulate formation of bone and mending of bone fractures. There are a number of bone morphogenic proteins, which are numbered starting with BMP-1. All the BMPs other than BMP-1 are members of a family of proteins that are structurally related to transforming growth factor beta (TGF-β), which is a cancer suppressing protein found in hematopoietic tissue, such as bone marrow. Bone morphogenic protein 2 (BMP-2) is one BMP related to TGF-β that stimulates growth of bone and cartilage. BMP-2 has been shown to stimulate migration of human osteoblasts, human marrow osteoblasts, and U2-OS cells. Lind et al., "Bone morphogenic protein-2 but not bone morphogenic protein-4 and -6 stimulates chemotactic migration of human osteoblasts, human marrow osteoblasts, and U2-OS cells," Bone, 18(1), 53-57 (1996). A recombinant human BMP-2 from CHO cells has been used in combination with a collagen sponge to stimulate fusion of spinal discs in spine fusion surgery, and has been credited with greatly improving the outcome of spine fusion surgery. Burkus, et al., "Radiographic Assessment of Interbody Fusion Using Recombinant Human Bone Morphogenetic Protein Type 2," Spine, 28(4), 372-377 (2003). BMP-4 has been implicated in bone healing, as it appears to be involved in post-fracture callus formation. Hitoshi Yaoita et al., "Expression of bone morphogenic proteins and rat distal-less homolog genes following rat femoral fracture," J. Bone and Mineral Metabolism, 18(2), 63-70 (2000). Osteogenic protein 1 (OP-1 or BMP-7) has been shown to stimulate bone growth when co-administered with demineralized bone in a human fibular defect. Geesink, et al., "Osteogenic activity of OP-1 bone morphogenic protein (BMP-7) in a human fibular defect," J. Bone Joint Surgery Br., 81(4), 710-718 (1999). Thus, BMP-2, BMP-4 and BMP-7 each induce endochondral bone formation in vivo. Ramoshebi et al., "Tissue engineering: TGF-β superfamily members and delivery systems in bone regeneration," Exp. Rev. Mol. Med., 2 Sep. 2002, http://www.expertreviews.org/02004969h.htm.

In some embodiments, the invention provides crosslinked tissue having at least one type of BMP (e.g. BMP-2, BMP-4 and/or BMP-7) conjugated to the tissue. In some embodiments, the tissue is internally crosslinked as well as being conjugated to the BMP. In some embodiments, the invention provides a method of making a chemically sterilized bioimplant having a BMP covalently linked to biological tissue. In some embodiments, the BMP is conjugated to the biological tissue prior to sterilization; in other embodiments the BMP is conjugated to the biological tissue after sterilization; in still further embodiments conjugation and sterilization occur in the same process step. In some preferred embodiments, the BMP and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the BMP and biological tissue are combined, frozen, lyophilized and then sterilized. In some preferred embodiments, the BMP retains biological activity while conjugated to the biological tissue and/or after placement within a host, regains biological activity after being released from the biological tissue.

Transforming Growth Factor-β

Transforming growth factor beta (TFG-β) is a transforming growth factor belonging to a superfamily of proteins including TGF-α and BMP-2. TGF-β plays an important role in bone remodeling, as it directly increases the steady-state rate of osteoblastic differentiation from osteoprogenitor cells, thereby increasing the final density of osteocytes embedded within bone matrix. Erlebacher, et al., "Osteoblastic responses to TGF-beta during bone remodeling," Mol. Biol. Cell., 9(7), 1903-1918 (1998). TGF-β exists in three isoforms (-β1, -β2 and -β3) in mammals. The TGF-β isoforms tested in Papio ursinus primates are powerful inducers of endochondral bone formation. Ramoshebi et al., 2002.

Thus, in some embodiments, invention provides sterilized tissue having at least one type of transforming growth factor (TGF) conjugated to the tissue. In some embodiments, the tissue is internally crosslinked as well as being conjugated to the TGF. In some embodiments, the invention provides a method of making a chemically sterilized bioimplant having a TGF covalently linked to biological tissue. In some embodiments, the TGF is conjugated to the biological tissue prior to sterilization; in other embodiments the TGF is conjugated to the biological tissue after sterilization; in still further embodiments conjugation and sterilization occur in the same process step. In some preferred embodiments, the TGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the TGF and biological tissue are combined, frozen, lyophilized and then sterilized. In some preferred embodiments, the TGF retains biological activity while conjugated to the biological tissue and/or after placement within a host, regains biological activity after being released from the biological tissue.

Fibroblast Growth Factor

The family of fibroblast growth factors (FGFs) exert growth-inducing effects during embryonic development. FGFs are responsible for determining which cells will become mesoderm, for inter alia limb outgrowth, as well as other developmental processes. In mammals there are nine FGF genes and four FGF receptors (FGFRs). The actual number of FGFs and FGFRs is actually larger, since there are multiple splicing forms for the FGF receptors and alternate translation initiation sites for the FGFs. Intravenous administration of human basic fibroblast growth factor (bFGF) stimulated osteoblast proliferation and new bone formation in various skeletal bones in both young and aged rats. Mayahara H, et al., "In vivo stimulation of endosteal bone formation by basic fibroblast growth factor in rats," Growth Factors, 9(1), 73-80 (1993).

Thus, in some embodiments, invention provides crosslinked and sterilized tissue having at least one type of FGF conjugated to the tissue. In some embodiments, the tissue is internally crosslinked as well as being conjugated to the FGF. In some embodiments, the invention provides a method of making a chemically sterilized bioimplant having a FGF covalently linked to biological tissue. In some embodiments, the FGF is conjugated to the biological tissue prior to sterilization; in other embodiments the FGF is conjugated to the biological tissue after sterilization; in still further embodiments conjugation and sterilization occur in the same process step. In some preferred embodiments, the FGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the FGF and biological tissue are combined, frozen, lyophilized and then sterilized. In some preferred embodiments, the FGF retains biological activity while conjugated to the biological tissue and/or after placement within a host, regains biological activity after being released from the biological tissue.

Platelet-Derived Growth Factor

Platelet-Derived Growth Factor (PDGF) is a dimeric glycoprotein composed of two A and/or B chains, giving rise to three isoforms (PDGF-AA, -AB and -BB). PDGF has been studied for chemotaxis, wound healing, and bone repair. Proliferative responses to PDGF action are exerted on many mesenchymal cell types. Other growth-related responses to PDGF include cytoskeletal rearrangement and increased polyphosphoinositol turnover. It appears that the primary effects of TGF-β are due to the induction, by TGF-β, of PDGF expression. Of the three forms, PDGF-BB is the most active in terms of bone cell effects, producing the greatest increase in cell replication in calvariae models. In osteoblast-enriched cultures derived from fetal calvariae, PDGF-BB is approximately eight times more mitogenic than PDGF-AA and three times more mitogenic than PDGF-AB. Osteoblasts incubated with PDGF-BB-treated matrices showed significantly increased proliferation over control matrices alone. Bateman et al., "Platelet-Derived Growth Factor Enhancement of Two Alloplastic Bone Matrices," J. Periodontology, 76(11), 1833-1841 (2005).

Thus, in some embodiments, the invention provides crosslinked and sterilized tissue having at least one type of PDGF (such as PDGF-BB) conjugated to the tissue. In some embodiments, the tissue is internally crosslinked as well as being conjugated to the PDGF. In some embodiments, the invention provides a method of making a chemically sterilized bioimplant having a PDGF covalently linked to biological tissue. In some embodiments, the PDGF is conjugated to the biological tissue prior to sterilization; in other embodiments the PDGF is conjugated to the biological tissue after sterilization; in still further embodiments conjugation and sterilization occur in the same process step. In some preferred embodiments, the PDGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the PDGF and biological tissue are combined, frozen, lyophilized and then sterilized. In some preferred embodiments, the PDGF retains biological activity while conjugated to the biological tissue and/or after placement within a host, regains biological activity after being released from the biological tissue.

Insulin-Like Growth Factors (IGFs)

As implied by its name, the insulin-like growth factors (IGFs) structurally resemble insulin. They have been shown to trigger responses in cells that are similar to those induced by insulin, such as mitogenesis. IGF-II is believed to be active in embryonic development, while IGF-I, which is primarily secreted by the liver, affects muscle, cartilage, bone, liver, kidney, nerves, skin and lungs. IGF-1 can regulate cell growth and development in cells. IGF-1 has been shown to protect myoblasts from apoptosis and to co-stimulate (along with horse serum) proliferation of myoblasts in vitro. Napier et al., "Insulin-like growth factor-I protects myoblasts from apoptosis but requires other factors to stimulate proliferation," J. Endocrinology, 163(1), 63-68 (1999). IGF-1 also stimulates uptake of 2-deoxyglucose and L-alanine (indicia of myoblast growth) at different development stages and had a significant effect on myoblast proliferation. Castillo et al., "Metabolic and mitogenic effects of IGF-1 and insulin on muscle cells of rainbow trout," Am. J. Physiol. Regul. Integr. Comp. Physiol., 286, R-935-R941 (2004). Depletion of IGF-1 in hypophysectomized rats decreased wound protein, DNA and hydroxyproline content of wounds by 50%, while infusion of IGF-1 to the hypophysectomized rats partially restored these indicia of wound healing. Mueller et al., "The effect of insulin-like growth factor I on wound healing variables and macrophages in rats," J. Am. Med. Assoc., 129(3), 1265-1270 (1994).

Thus, in some embodiments, invention provides crosslinked and sterilized tissue having at least one type of an IGF (such as IGF-I) conjugated to the tissue. In some embodiments, the tissue is internally crosslinked as well as being conjugated to the IGF. In some embodiments, the invention provides a method of making a chemically sterilized bioimplant having a IGF covalently linked to biological tissue. In some embodiments, the IGF is conjugated to the biological tissue prior to sterilization; in other embodiments the IGF is conjugated to the biological tissue after sterilization; in still further embodiments conjugation and sterilization occur in the same process step. In some preferred embodiments, the IGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the IGF and biological tissue are combined, frozen, lyophilized and then sterilized. In some preferred embodiments, the IGF retains biological activity while conjugated to the biological tissue and/or after placement within a host, regains biological activity after being released from the biological tissue.

Cartilage-Derived Growth Factor (CDGF)

Cartilage-derived growth factor (CDGF) is a cationic polypeptide of approximately 18,000 mol wt. Studies have shown that CDGF stimulates the proliferation of cultured mouse fibroblasts as well as chondrocytes and endothelial cells from various sources. CDGF has also shown to stimulate dose-dependently the accumulation of DNA and collagen by rat embryo fibroblasts and a population of fibroblasts derived from granulation tissue. CDGF has also been shown to stimulate the proliferation of cultured bovine capillary endothelial cells dose-dependently. Davidson et al., "Accelerated wound repair, cell proliferation, and collagen accumulation are produced by a cartilage-derived growth factor," J. Cell. Biol., 100(4), 1219-1227 (1985). Cartilage-derived growth factor (CDGF) is a protein closely related to basic fibroblast growth factor known to have both mitogenic and chemokinetic properties in microvascular endothelial cells. CDGF is also known to play a role in angiogenesis and acceleration of wound repair.

Thus, in some embodiments, invention provides crosslinked and sterilized tissue having at least one type of CDGF conjugated to the tissue. In some embodiments, the tissue is internally crosslinked as well as being conjugated to the CDGF. In some embodiments, the invention provides a method of making a chemically sterilized bioimplant having a CDGF covalently linked to biological tissue. In some embodiments, the CDGF is conjugated to the biological tissue prior to sterilization; in other embodiments the CDGF is conjugated to the biological tissue after sterilization; in still further embodiments conjugation and sterilization occur in the same process step. In some preferred embodiments, the CDGF and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the CDGF and biological tissue are combined, frozen, lyophilized and then sterilized. In some preferred embodiments, the CDGF retains biological activity while conjugated to the biological tissue and/ or after placement within a host, regains biological activity after being released from the biological tissue.

Glycosaminoglycans (GAGs)

Glycosaminoglycans are linear polymers of amino sugar uronic acid disaccharides and form the saccharide portion of proteoglycans. Glycosaminoglycans interact with various proteins and can participate in matrix organization, cell adhesion, differentiation and tissue growth. Some glycosaminoglycans, such as hyaluronan have been suggested as agents to enhance wound healing especially after surgery. For example, collagen-glycosaminoglycan blended nanofibrous scaffolds have been developed as mimetics of the native extracellular matrix. Incorporation of the collagen-glycosaminoglycan scaffold was found to promote cell growth in vitro. Zhong et al., "Formation of Collagen-Glycosaminoglycan Blended Nanofibrous Scaffolds and Their Biological Properties," Biomacromolecules, 6(6), 2998-3004 (2005). Thus, in some embodiments, the invention provides crosslinked biological tissue having covalently bonded to it one or more glycosaminoglycans, such as hyaluronan, chondroitin sulfate, keratin sulfate, dermatan sulfate, heparin or heparan sulfate. The invention also provides methods of making such glycosaminoglycan-linked crosslinked biological tissue. Such methods include contacting a biological tissue with the glycosaminoglycan and a suitable conjugating agent under conditions suitable to form a covalent link between the glycosaminoglycan and the biological tissue. Where necessary, an ester or amide bond is broken in the glycosaminoglycan and the resulting moiety is contacted with the biological tissue and conjugating agent.

Thus, in some embodiments, invention provides crosslinked and sterilized tissue having at least one type of GAG, such as hyaluronan, chondroitin sulfate, keratin sulfate, dermatan sulfate, heparin or heparan sulfate, conjugated to the tissue. In some embodiments, the tissue is internally crosslinked as well as being conjugated to the GAG. In some embodiments, the invention provides a method of making a chemically sterilized bioimplant having a GAG covalently linked to biological tissue. In some embodiments, the GAG is conjugated to the biological tissue prior to sterilization; in other embodiments the GAG is conjugated to the biological tissue after sterilization; in still further embodiments conjugation and sterilization occur in the same process step. In some preferred embodiments, the GAG and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the GAG and biological tissue are combined, frozen, lyophilized and then sterilized. In some preferred embodiments, the GAG retains biological activity while conjugated to the biological tissue and/or after placement within a host, regains biological activity after being released from the biological tissue.

Antibiotics

Bacterial infection, especially by ubiquitous bacteria such as Staphylococcus aureus (S. aureus), often interfere with the healing process. Thus it is often desirable to treat a postoperative patient with one or more antibiotics. For example, the efficacy of ticarcillin and clavulanic acid has been tested against S. areus infection in an experimental model of endocarditis in order to demonstrate the clinical potential of the combination of ticarcillin (a β-lactam antibiotic) and clavulanic acid (a β-lactamase inhibitor) in the prophylaxis or therapy of severe staphylococcal infections. Catherall, et al., "Efficacy of ticarcillin-clavulanic acid for treatment of experimental Staphylococcus aureus endocarditis in rats," Antimicrob. Agents and Chemother., 36(2), 458-462 (1992). Clavulanic acid has also been combined with amoxicillin for treatment of β-lactamase generating bacterial infections. U.S. Pat. Nos. 4,525,352, 4,529,720, 4,560,552. Despite the effectiveness of various antibiotic treatments, it is considered desirable to avoid systemic dosing of antibiotics, where possible, in order to avoid or ameliorate the toxic side effects of certain antibiotic drugs, and to reduce the likelihood of developing antibiotic resistant strains of bacteria. Thus, the present invention address this problem by providing bioimplants and methods for making those bioimplants wherein at least one antibiotic is covalently attached to the bioimplant.

Various families of structurally-related antibiotics have been developed and are considered useful in preparing embodiments of bioimplants of the present invention. Such families of antibiotics include the aminoglycosides, the amphenicols, the ansamycins, the β-lactams, the lincosamides, the macrolides, the polypeptide antibiotics, the tetracyclines, cycloserine, mupirocin, tuberin and the synthetic antibacterial compounds such as 2,4-diaminopyrimidines, the nitrofurans, the quinolones, the sulfonamides, the sulfones, clofoctol, hexedine, methenamine, nitroxoline, taurolidine and xibernol. Thus, in some embodiments, the invention provides crosslinked biological tissue having covalently bonded to it one or more members of the family of antibiotics through a suitable linker. The invention also provides methods of making such antibiotic-linked crosslinked biological tissue. Such methods include contacting a biological tissue with the antibiotic and a suitable conjugating agent under conditions suitable to form a covalent link between the antibiotic and the biological tissue.

Thus, in some embodiments, invention provides crosslinked and sterilized tissue having at least one type of antibiotic conjugated to the tissue. In some embodiments, the tissue is internally crosslinked as well as being conjugated to the antibiotic. In some embodiments, the invention provides a method of making a chemically sterilized bioimplant having an antibiotic covalently linked to biological tissue. In some embodiments, the antibiotic is conjugated to the biological tissue prior to sterilization; in other embodiments the antibiotic is conjugated to the biological tissue after sterilization; in still further embodiments conjugation and sterilization occur in the same process step. In some preferred embodiments, the antibiotic and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the antibiotic and biological tissue are combined, frozen, lyophilized and then sterilized. In some preferred embodiments, the antibiotic retains biological activity while conjugated to the biological tissue and/or after placement within a host, regains biological activity after being released from the biological tissue.

Aminoglycosides

One class of antibiotics considered useful in preparing a bioimplant of the present invention is the aminoglycosides. Suitable aminoglycosides include amikacin, apramycin, arbekacin, bambermycins, butirosin, dibekacin, dihydrostreptomycin, fortimicins, gentamicin, isepamicin, kanamycin (A, B or C), micronomicin, neomycin (A, B or C), netilmicin, paromomycin, ribostamycin, sisomicin, spectinomycin, streptomycin, tobramycin and trospectomycin. Thus, in some embodiments, the invention provides crosslinked biological tissue having covalently bonded to it one or more of the foregoing aminoglycoside antibiotics through a suitable linker. The invention also provides methods of making such aminoglycoside antibiotic-linked crosslinked biological tissue. Such methods include contacting a biological tissue with the aminoglycoside and a suitable conjugating agent under conditions suitable to form a covalent link between the aminoglycoside antibiotic and the biological tissue. Where necessary, an ester or amide bond may be broken in the aminoglycoside antibiotic and the resulting moiety is contacted with the biological tissue and conjugating agent.

Thus, in some embodiments, invention provides crosslinked and sterilized tissue having at least one type of aminoglycoside conjugated to the tissue. In some embodiments, the tissue is internally crosslinked as well as being conjugated to the aminoglycoside. In some embodiments, the invention provides a method of making a chemically sterilized bioimplant having a aminoglycoside covalently linked to biological tissue. In some embodiments, the aminoglycoside is conjugated to the biological tissue prior to sterilization; in other embodiments the aminoglycoside is conjugated to the biological tissue after sterilization; in still further embodiments conjugation and sterilization occur in the same process step. In some preferred embodiments, the aminoglycoside and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the aminoglycoside and biological tissue are combined, frozen, lyophilized and then sterilized. In some preferred embodiments, the aminoglycoside retains biological activity while conjugated to the biological tissue and/or after placement within a host, regains biological activity after being released from the biological tissue.

β-Lactams

A variety of β-lactam antibiotics have been developed and are considered suitable for preparing the bioimplants according to the invention. Suitable β-lactam antibiotics include carbacephems, carbapenems, cephalosporins, cephamycins, monobactams, oxacephems, penicillins and ritapenem.

Suitable carbacephems include loracarbef.

Suitable carbapenems include biapenem, imipenem, meropenem and panipenem.

Suitable cephalosporins include cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsoludin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephamycins, cephapirin sodium, cephradine and pivcefalexin.

Suitable cephamycins include cefbuperazone, cefmetazole, cefminox, cefotetan and cefoxitin. Suitable monobactams include aztreonam, carumonam and tigemonam.

Suitable oxacephems include flomoxef and moxalactam. Suitable penicillins include amdinocillin, amoxicillin, ampicillin, apalcillin, aspoxicillin, azidocillin, azlocillin, bacampicillin, benzylpenicillinic acid, carbenicillin, caridacillin, clometocillin, cloxacillin, cyclacillin, dicloxacillin, epicillin, fenbenicillin, floxacillin, hetacillin, lenampicillin, metampicillin, methicillin, mezlocillin, nafcillin, oxacillin, penamecillin, penethamate, penicillin G, penicillin N, penicillin O, penicillin V, penimepicycline, phenethicillin, piperacillin, pivampicillin, propicillin, quinacillin, sulbenicillin, sultamicillin, talampicillin, temocillin and ticarcillin.

Thus, in some embodiments, invention provides crosslinked and sterilized tissue having at least one type of β-lactam conjugated to the tissue. In some embodiments, the tissue is internally crosslinked as well as being conjugated to the β-lactam. In some embodiments, the invention provides a method of making a chemically sterilized bioimplant having a β-lactam covalently linked to biological tissue. In some embodiments, the β-lactam is conjugated to the biological tissue prior to sterilization; in other embodiments the β-lactam is conjugated to the biological tissue after sterilization; in still further embodiments conjugation and sterilization occur in the same process step. In some preferred embodiments, the β-lactam and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the β-lactam and biological tissue are combined, frozen, lyophilized and then sterilized. In some preferred embodiments, the β-lactam retains biological activity while conjugated to the biological tissue and/or after placement within a host, regains biological activity after being released from the biological tissue.

Lincosamides

Lincosamides that are considered suitable for preparing the bioimplants according to the invention include clindamycin and lincomycin. Thus, in some embodiments, the invention provides crosslinked biological tissue having covalently bonded to it one or more of the foregoing lincosamide antibiotics through a suitable linker. The invention also provides methods of making such lincosamide antibiotic-linked crosslinked biological tissue. Such methods include contacting a biological tissue with the lincosamide and a suitable conjugating agent under conditions suitable to form a covalent link between the lincosamide antibiotic and the biological tissue. Where necessary, the present invention provides such methods wherein an ester or amide bond is first cleaved in the lincosamide and then the resulting lincosamide is linked to the biological tissue to form the bioimplant of the invention.

Thus, in some embodiments, invention provides crosslinked and sterilized tissue having at least one type of lincosamide conjugated to the tissue. In some embodiments, the tissue is internally crosslinked as well as being conjugated to the lincosamide. In some embodiments, the invention provides a method of making a chemically sterilized bioimplant having a lincosamide covalently linked to biological tissue. In some embodiments, the lincosamide is conjugated to the biological tissue prior to sterilization; in other embodiments the lincosamide is conjugated to the biological tissue after sterilization; in still further embodiments conjugation and sterilization occur in the same process step. In some preferred embodiments, the lincosamide and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the lincosamide and biological tissue are combined, frozen, lyophilized and then sterilized. In some preferred embodiments, the lincosamide retains biological activity while conjugated to the biological tissue and/or after placement within a host, regains biological activity after being released from the biological tissue.

Macrolides

A variety of macrolides have been developed and are considered suitable for preparing the bioimplants according to the invention. Suitable macrolides include azithromycin, carbomycin, clarithromycin, dirithromycin, erythromycin, josamycin, leucomycins, midecamycins, miokamycin, oleandomycin, primycin, rokitamycin, rosaramicin, roxithromycin, spiramycin and troleandomycin. Thus, in some embodiments, the invention provides crosslinked biological tissue having covalently bonded to it one or more of the foregoing macrolide antibiotics through a suitable linker. The invention also provides methods of making such macrolide antibiotic-linked crosslinked biological tissue. Such methods include contacting a biological tissue with the macrolide and a suitable conjugating agent under conditions suitable to form a covalent link between the macrolide antibiotic and the biological tissue. Where necessary, the present invention provides such methods wherein an ester or amide bond is first cleaved in the macrolide and then the resulting macrolide is linked to the biological tissue to form the bioimplant of the invention.

Thus, in some embodiments, invention provides crosslinked and sterilized tissue having at least one type of macrolide conjugated to the tissue. In some embodiments, the tissue is internally crosslinked as well as being conjugated to the macrolide. In some embodiments, the invention provides a method of making a chemically sterilized bioimplant having a macrolide covalently linked to biological tissue. In some embodiments, the macrolide is conjugated to the biological tissue prior to sterilization; in other embodiments the macrolide is conjugated to the biological tissue after sterilization; in still further embodiments conjugation and sterilization occur in the same process step. In some preferred embodiments, the macrolide and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the macrolide and biological tissue are combined, frozen, lyophilized and then sterilized. In some preferred embodiments, the macrolide retains biological activity while conjugated to the biological tissue and/or after placement within a host, regains biological activity after being released from the biological tissue.

Polypeptides

A variety of polypeptides have been developed and are considered suitable for preparing the bioimplants according to the invention. Suitable polypeptides include amphomycin, bacitracin, capreomycin, colistin, enduracidin, enviomycin, polymyxin, ristocetin, teicoplanin, thiostrepton, tuberactinomycin, tyrocidine and vancomycin. Thus, in some embodiments, the invention provides crosslinked biological tissue having covalently bonded to it one or more of the foregoing polypeptide antibiotics through a suitable linker. The invention also provides methods of making such polypeptide antibiotic-linked crosslinked biological tissue. Such methods include contacting a biological tissue with the polypeptide and a suitable conjugating agent under conditions suitable to form a covalent link between the polypeptide antibiotic and the biological tissue. Where necessary, the present invention provides such methods wherein an ester or amide bond is first cleaved in the polypeptide and then the resulting polypeptide is linked to the biological tissue to form the bioimplant of the invention.

Thus, in some embodiments, invention provides crosslinked and sterilized tissue having at least one type of adjunct polypeptide conjugated to the tissue. In some embodiments, the tissue is internally crosslinked as well as being conjugated to the polypeptide. In some embodiments, the invention provides a method of making a chemically sterilized bioimplant having a polypeptide covalently linked to biological tissue. In some embodiments, the polypeptide is conjugated to the biological tissue prior to sterilization; in other embodiments the polypeptide is conjugated to the biological tissue after sterilization; in still further embodiments conjugation and sterilization occur in the same process step. In some preferred embodiments, the polypeptide and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the polypeptide and biological tissue are combined, frozen, lyophilized and then sterilized. In some preferred embodiments, the polypeptide retains biological activity while conjugated to the biological tissue and/or after placement within a host, regains biological activity after being released from the biological tissue.

Tetracyclines

A variety of tetracyclines have been developed and are considered suitable in preparing the bioimplants according to the invention. Suitable tetracyclines include apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline and tetracycline. Thus, in some embodiments, the invention provides crosslinked biological tissue having covalently bonded to it one or more of the foregoing tetracycline antibiotics through a suitable linker. The invention also provides methods of making such tetracycline antibiotic-linked crosslinked biological tissue. Such methods include contacting a biological tissue with the tetracycline and a suitable conjugating agent under conditions suitable to form a covalent link between the tetracycline antibiotic and the biological tissue. Where necessary, the present invention provides such methods wherein an ester or amide bond is first cleaved in the tetracycline and then the resulting tetracycline is linked to the biological tissue to form the bioimplant of the invention.

Thus, in some embodiments, invention provides crosslinked and sterilized tissue having at least one type of tetracycline conjugated to the tissue. In some embodiments, the tissue is internally crosslinked as well as being conjugated to the tetracycline. In some embodiments, the invention provides a method of making a chemically sterilized bioimplant having a tetracycline covalently linked to biological tissue. In some embodiments, the tetracycline is conjugated to the biological tissue prior to sterilization; in other embodiments the tetracycline is conjugated to the biological tissue after sterilization; in still further embodiments conjugation and sterilization occur in the same process step. In some preferred embodiments, the tetracycline and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the tetracycline and biological tissue are combined, frozen, lyophilized and then sterilized. In some preferred embodiments, the tetracycline retains biological activity while conjugated to the biological tissue and/or after placement within a host, regains biological activity after being released from the biological tissue.

2,4-Diaminopyrimidines

A variety of 2,4-diaminopyrimidines have been developed and are considered suitable for preparing the bioimplants according to the invention. Suitable 2,4-diaminopyrimidines include brodimoprim, tetroxoprim and trimethoprim. Thus, in some embodiments, the invention provides crosslinked biological tissue having covalently bonded to it one or more of the foregoing 2,4-diaminopyrimidines antibiotics through a suitable linker. The invention also provides methods of making such 2,4-diaminopyrimidines antibiotic-linked crosslinked biological tissue. Such methods include contacting a biological tissue with the 2,4-diaminopyrimidines and a suitable conjugating agent under conditions suitable to form a covalent link between the 2,4-diaminopyrimidines antibiotic and the biological tissue. Where necessary, the present invention provides such methods wherein an ester or amide bond is first cleaved in the 2,4-diaminopyrimidines and then the resulting 2,4-diaminopyrimidines is linked to the biological tissue to form the bioimplant of the invention.

Thus, in some embodiments, invention provides crosslinked and sterilized tissue having at least one type of 2,4-diaminopyrimidine conjugated to the tissue. In some embodiments, the tissue is internally crosslinked as well as being conjugated to the 2,4-diaminopyrimidine. In some embodiments, the invention provides a method of making a chemically sterilized bioimplant having a 2,4-diaminopyrimidine covalently linked to biological tissue. In some embodiments, the 2,4-diaminopyrimidine is conjugated to the biological tissue prior to sterilization; in other embodiments the 2,4-diaminopyrimidine is conjugated to the biological tissue after sterilization; in still further embodiments conjugation and sterilization occur in the same process step. In some preferred embodiments, the 2,4-diaminopyrimidine and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the 2,4-diaminopyrimidine and biological tissue are combined, frozen, lyophilized and then sterilized. In some preferred embodiments, the 2,4-diaminopyrimidine retains biological activity while conjugated to the biological tissue and/or after placement within a host, regains biological activity after being released from the biological tissue.

Quinolones and Analogs of Quinolones

A variety of quinolones and analogs of quinolones have been developed and are considered suitable for preparing the bioimplants according to the invention. Suitable quinolone and quinolone analog adjuncts within the scope of the present invention include: cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin and trovafloxacin. Thus, in some embodiments, the invention provides crosslinked biological tissue having covalently bonded to it one or more of the foregoing quinolones and analogs of quinolones antibiotics through a suitable linker. The invention also provides methods of making such quinolones and analogs of quinolones antibiotic-linked crosslinked biological tissue. Such methods include contacting a biological tissue with the quinolones and analogs of quinolones and a suitable conjugating agent under conditions suitable to form a covalent link between the quinolones and analogs of quinolones antibiotic and the biological tissue. Where necessary, the present invention provides such methods wherein an ester or amide bond is first cleaved in the macrolide and then the resulting quinolones and analogs of quinolones is linked to the biological tissue to form the bioimplant of the invention.

Thus, in some embodiments, invention provides crosslinked and sterilized tissue having at least one type of quinolone or quinolone analog conjugated to the tissue. In some embodiments, the tissue is internally crosslinked as well as being conjugated to the quinolone or quinolone analog. In some embodiments, the invention provides a method of making a chemically sterilized bioimplant having a quinolone or quinolone analog covalently linked to biological tissue. In some embodiments, the quinolone or quinolone analog is conjugated to the biological tissue prior to sterilization; in other embodiments the quinolone or quinolone analog is conjugated to the biological tissue after sterilization; in still further embodiments conjugation and sterilization occur in the same process step. In some preferred embodiments, the quinolone or quinolone analog and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the quinolone or quinolone analog and biological tissue are combined, frozen, lyophilized and then sterilized. In some preferred embodiments, the quinolone or quinolone analog retains biological activity while conjugated to the biological tissue and/or after placement within a host, regains biological activity after being released from the biological tissue.

Sulfonamides

A variety of sulfonamides have been developed and are considered suitable for in preparing the bioimplants according to the invention. Suitable sulfonamides include acetylsulfamethoxypyrazine, benzylsulfamide, chloramine-B, chloramine-T, $N^4$-β-D-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $N^4$-sulfanilylsulfanilamide, sulfanilylurea, N-sulfanilyl-3,4-xylamide, sulfaperine, sulfaphenazole, sulfaproxyline, sulfapyrazine, sulfapyridine, sulfaquinoxaline, sulfasomizole, sulfasymazine, sulfathiazole, sulfathiourea, sulfatolamide, sulfazamet, sulfisomidine and sulfisoxazole. Thus, in some embodiments, the invention provides crosslinked biological tissue having covalently bonded to it one or more of the foregoing sulfonamide antibiotics through a suitable linker. The invention also provides methods of making such sulfonamide antibiotic-linked crosslinked biological tissue. Such methods include contacting a biological tissue with the sulfonamide and a suitable conjugating agent under conditions suitable to form a covalent link between the sulfonamide antibiotic and the biological tissue. Where necessary, the present invention provides such methods wherein an ester or amide bond is first cleaved in the sulfonamide and then the resulting sulfonamide is linked to the biological tissue to form the bioimplant of the invention.

Thus, in some embodiments, invention provides crosslinked and sterilized tissue having at least one type of sulfonamide conjugated to the tissue. In some embodiments, the tissue is internally crosslinked as well as being conjugated to the sulfonamide. In some embodiments, the invention provides a method of making a chemically sterilized bioimplant having a sulfonamide covalently linked to biological tissue. In some embodiments, the sulfonamide is conjugated to the biological tissue prior to sterilization; in other embodiments the sulfonamide is conjugated to the biological tissue after sterilization; in still further embodiments conjugation and sterilization occur in the same process step. In some preferred embodiments, the sulfonamide and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the sulfonamide and biological tissue are combined, frozen, lyophilized and then sterilized. In some preferred embodiments, the sulfonamide retains biological activity while conjugated to the biological tissue and/or after placement within a host, regains biological activity after being released from the biological tissue.

Sulfones

A variety of sulfones have been developed and are considered suitable for preparing the bioimplants according to the invention. Suitable sulfones include acediasulfone, acetosulfone sodium, dapsone, diathymosulfone, glucosulfone, solasulfone, succisulfone, sulfanilic acid, 2-p-sulfanilylanilinoethanol, p-sulfanilylbenylamine and thiazolsulfone. Thus, in some embodiments, the invention provides crosslinked biological tissue having covalently bonded to it one or more of the foregoing sulfone antibiotics through a suitable linker. The invention also provides methods of making such sulfone antibiotic-linked crosslinked biological tissue. Such methods include contacting a biological tissue with the sulfone and a suitable conjugating agent under conditions suitable to form a covalent link between the sulfone antibiotic and the biological tissue. Where necessary, the present invention provides such methods wherein an ester or amide bond is first cleaved in the sulfone and then the resulting moiety is linked to the biological tissue to form the bioimplant of the invention.

Thus, in some embodiments, invention provides crosslinked and sterilized tissue having at least one type of sulfone conjugated to the tissue. In some embodiments, the tissue is internally crosslinked as well as being conjugated to the sulfone. In some embodiments, the invention provides a method of making a chemically sterilized bioimplant having a sulfone covalently linked to biological tissue. In some embodiments, the sulfone is conjugated to the biological tissue prior to sterilization; in other embodiments the sulfone is conjugated to the biological tissue after sterilization; in still further embodiments conjugation and sterilization occur in the same process step. In some preferred embodiments, the sulfone and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the sulfone and biological tissue are combined, frozen, lyophilized and then sterilized. In some preferred embodiments, the sulfone retains biological activity while conjugated to the biological tissue and/or after placement within a host, regains biological activity after being released from the biological tissue.

Other Synthetic Antibiotics

A variety of other synthetic antibiotics have been developed and are considered suitable for preparing the bioimplants according to the invention. Suitable antibiotics include clofoctol, hexedine, methenamine, nitroxoline, taurolidine and xibornol. Thus, in some embodiments, the invention provides crosslinked biological tissue having covalently bonded to it one or more of the foregoing antibiotics through a suitable linker. The invention also provides methods of making such antibiotic-linked crosslinked biological tissue. Such methods include contacting a biological tissue with the antibiotic and a suitable conjugating agent under conditions suitable to form a covalent link between the antibiotic and the biological tissue. Where necessary, the present invention provides such methods wherein an ester or amide bond is first cleaved in the antibiotic and then the resulting moiety is linked to the biological tissue to form the bioimplant of the invention.

Thus, in some embodiments, invention provides crosslinked and sterilized tissue having at least one type of a synthetic antibiotic conjugated to the tissue. In some embodiments, the tissue is internally crosslinked as well as being conjugated to the synthetic antibiotic. In some embodiments, the invention provides a method of making a chemically sterilized bioimplant having a synthetic antibiotic covalently linked to biological tissue. In some embodiments, the synthetic antibiotic is conjugated to the biological tissue prior to sterilization; in other embodiments the synthetic antibiotic is conjugated to the biological tissue after sterilization; in still further embodiments conjugation and sterilization occur in the same process step. In some preferred embodiments, the synthetic antibiotic and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the synthetic antibiotic and biological tissue are combined, frozen, lyophilized and then sterilized. In some preferred embodiments, the synthetic antibiotic retains biological activity while conjugated to the biological tissue and/or after placement within a host, regains biological activity after being released from the biological tissue.

Antibacterial Adjunctives

A variety of antibacterial adjunctives have been developed and are considered suitable for preparing the bioimplants according to the invention. Suitable antibiotic adjunctives include the β-lactamase inhibitors, which, when co-administered with one or more β-lactam antibiotics enhance the efficacy of such β-lactam antibiotics in the treatment of bacterial infections with β-lactam antibiotic-resistant bacteria, such as those that express β-lactamase. Suitable β-lactamase inhibitors include clavulanic acid, sulbactam, sultamicillin and tazobactam. Thus, in some embodiments, the invention provides crosslinked biological tissue having covalently bonded to it one or more of the foregoing antibiotic adjuncts through a suitable linker. The invention also provides methods of making such antibiotic adjunct-linked crosslinked biological tissue. Such methods include contacting a biological tissue with the antibiotic adjunct and a suitable conjugating agent under conditions suitable to form a covalent link between the antibiotic adjunct and the biological tissue. Where necessary, the present invention provides such methods wherein an ester or amide bond is first cleaved in the antibiotic adjunct and then the resulting moiety is linked to the biological tissue to form the bioimplant of the invention.

Thus, in some embodiments, invention provides crosslinked and sterilized tissue having at least one type of antibiotic adjunctive agent (such as clavulanic acid) conjugated to the tissue. In some embodiments, the tissue is internally crosslinked as well as being conjugated to the antibiotic adjunctive. In some embodiments, the invention provides a method of making a chemically sterilized bioimplant having a antibiotic adjunctive covalently linked to biological tissue. In some embodiments, the antibiotic adjunctive is conjugated to the biological tissue prior to sterilization; in other embodiments the antibiotic adjunctive is conjugated to the biological tissue after sterilization; in still further embodiments conjugation and sterilization occur in the same process step. In some preferred embodiments, the antibiotic adjunctive and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the antibiotic adjunctive and biological tissue are combined, frozen, lyophilized and then sterilized. In some preferred embodiments, the antibiotic adjunctive retains biological activity while conjugated to the biological tissue and/or after placement within a host, regains biological activity after being released from the biological tissue.

Small Peptides

In some embodiments, the invention provides a bioimplant having conjugated thereto an adjunct molecule that is a small peptide. The dividing line between proteins and small peptides is of necessity arbitrary; and in general the methods used to conjugate proteins, such as growth factors, to a biological tissue apply equally well to small peptides. In general, a small peptide is considered one having fewer than 50, 45, 40, 35, 30 or 25 amino acids. Aside from the antibiotic small peptides listed above, specific peptides contemplated within the scope of the present invention include the magainins (e.g. magainin I and magainin II), which are 22 amino acid antimicrobial peptides obtained from *Xenopus laevis*. The magainins are lysine rich, and thus readily form amide bonds with appropriate carboxylic acid, amino acid or carboxylic acid anhydride reagents.

Thus, in some embodiments, invention provides crosslinked and sterilized tissue having at least one type of small peptide conjugated to the tissue. In some embodiments, the tissue is internally crosslinked as well as being conjugated to the small peptide. In some embodiments, the invention provides a method of making a chemically sterilized bioimplant having a small peptide covalently linked to biological tissue. In some embodiments, the small peptide is conjugated to the biological tissue prior to sterilization; in other embodiments the small peptide is conjugated to the biological tissue after sterilization; in still further embodiments conjugation and sterilization occur in the same process step. In some preferred embodiments, the small peptide and the biological tissue are combined and then sterilized with a sterilizing agent, such as a water soluble carbodiimide (e.g. EDC), optionally in the presence of a penetration enhancer, such as an alkanol (e.g. isopropanol). In some particularly preferred embodiments, the small peptide and biological tissue are combined, frozen, lyophilized and then sterilized. In some preferred embodiments, the small peptide retains biological activity while conjugated to the biological tissue and/or after placement within a host, regains biological activity after being released from the biological tissue. In some embodiments, the peptide conjugated to the biological tissue is one of the following: magainin I, magainin II, an Arg-Asp-Gly (RGD) peptide, an osteogenic peptide (such as parathyroid hormone related peptide (PTHrP), an osteogenic growth peptide (OPG), TP 508, P-15, etc.) or other growth modulating and/or cell differentiation-inducing peptides. In some embodiments, two or more peptides of the following group are conjugated to the biological tissue: magainin I, magainin II, an Arg-Asp-Gly (RGD) peptide, an osteogenic peptide (such as parathyroid hormone related peptide (PTHrP), an osteogenic growth peptide (OPG), TP 508, P-15, etc.) or other growth modulating and/or cell differentiation-inducing peptides.

Processes of Making a Bioimplant of the Invention

The present invention provides methods of making sterilized bioimplants having adjunct molecules linked thereto. The methods comprise conjugating an adjunct molecule to a biological tissue and sterilizing the biological tissue. In general, the conjugation and sterilization can take place in any order, or preferably simultaneously, although it is preferred that a sterilization step be the ultimate step prior to packaging the bioimplant, e.g. in a sealed polymer bag.

The sterilization is carried out in the presence of a chemical sterilizing agent, optionally in the presence of a sterilization enhancer and/or a penetration enhancer. In some embodiments, the preferred sterilization agent is a water soluble sterilizing agent, in particular a water-soluble carbodiimide, such as EDC. The sterilizing agent is preferably used in a concentration of at least about 1 mM, especially from about 5 mM to about 100 mM, more specifically from about 15 mM to about 50 mM, and most preferably from abut 20 mM to about 40 mM.

In some embodiments, the sterilizing agent is accompanied by a sterilization enhancer, such as N-hydroxysuccinimide (NHS) or 2-sulfo-N-hydroxysuccinimide (Sulfo-NHS). In some embodiments, the ratio of sterilization enhancer to sterilizing agent is in the range of about 1:100 to about 1:1, especially about 1:50 to 1:1, preferably in the range of about 1:20 to 1:1, and more preferably in the range of about 1:10 to 1:1. Particularly, the sterilization enhancer is at a concentration of about 0.5 mM to about 30 mM, preferably about 1 mM to about 5 mM.

In some embodiments, it is considered preferable to use a penetration enhancer in the sterilization process in order to enhance penetration of the sterilizing agent into the microbes to be killed. Suitable penetration enhancers are alkanols, such as short-chained or small-ringed alkanols, e.g. methanol, ethanol, isopropanol, n-propanol, isobutanol, n-butanol, s-butanol, t-butanol, n-pentanol, n-hexanol, cyclopropanol, cyclobutanol, cyclopentanol, cyclohexanol, cycloheptanol, cyclooctanol or combinations of any of the foregoing. In this regard, isopropanol is especially preferred. In some embodiments, preferred concentrations of penetration enhancer are about 1% (vol/vol) to about 50% (vol/vol), especially about 5% (vol/vol) to about 40% (vol/vol) and even more preferably about 10%, about 15%, about 20%, about 30%, about 35% or about 40% (vol/vol). A particularly preferred penetration enhancer is about 20% (vol/vol) of isopropanol.

In some preferred embodiments, the sterilization and conjugation are carried out simultaneously in the presence of a sterilizing agent, and preferably in the presence of a sterilization enhancer and/or a penetration enhancer. Although within some embodiments of the invention there may be used a bifunctional linking molecule as a conjugating agent, in some preferred embodiments the sterilization agent and optionally sterilization enhancer and/or penetration enhancer are considered sufficient to conjugate the adjunct to the biological tissue, sterilize the combined tissue and adjunct, and optionally crosslink the biological tissue. In some preferred embodiments, the biological tissue and adjunct are combined to form an intermediate, which is then frozen and lyophilized. The resulting lyophilized intermediate is then contacted with the sterilizing agent and optionally a sterilization enhancer and/or a penetration enhancer (with or, preferably without, a conjugating agent). In some embodiments, the biological tissue is frozen and lyophilized. The lyophilized intermediate is then contacted with a solution containing adjunct molecule and sterilizing agent and optionally one or more member of the group of sterilizing enhancers, penetration enhancers and/or bifunctional conjugating agent.

In some embodiments, the adjunct is conjugated to the biological tissue prior to sterilization. In such embodiments, the biological tissue and adjunct are contacted with a conjugation solution to affect conjugation. The conjugation solution comprises a conjugating agent, such as a water soluble carbodiimide or NHS. The conjugation solution also optionally comprises a conjugation enhancer, such as Sulfo-NHS. In addition, the conjugation solution also optionally comprises a bifunctional conjugating agent, such as a lower alkane diamine, diacid or amino acid.

Uses of the Bioimplants of the Invention

The bioimplants of the invention are especially advantageous in that they promote post-operative tissue healing, remodeling, growth and/or regrowth. In some embodiments, the bioimplants present on their surface or release adjuncts that directly stimulate tissue healing, remodeling, growth and/or regrowth. In some embodiments, the bioimplants present on their surface or release adjuncts, which indirectly promote tissue healing, remodeling, growth and/or regrowth by inhibiting the bioactivity of one or more microbes in the vicinity of the bioimplant, thereby allowing the recipient's body to heal, remodel, grow or regrow tissue without, or with attenuated, interference from one or more microbes.

In some embodiments, the bioimplants directly promote post-operative tissue healing, remodeling, growth and/or regrowth by presenting on their surface or releasing one or more proteins, such as active growth factors, which recruit to the bioimplant host molecules or cells that promote tissue healing, remodeling, growth and/or regrowth. In particular embodiments, the bioimplants present on their surface or release a TGF-β, PDGF, FGF, IGF, CDGF or a BMP, which promote tissue healing, remodeling, growth and/or regrowth by recruiting to the site of the bioimplant one or more molecules or cells that effect tissue healing, remodeling, growth or regrowth in the recipient.

In some embodiments, the bioimplants indirectly promote post-operative tissue healing by interfering with one or more microbes that would otherwise interfere with tissue healing, remodeling, growth and/or regrowth. The bioimplants thus present on their surface or release into the environment of the bioimplant one or more adjuncts that interfere with microbial activity in at least one microbe, such as *Staphylococcus aureus*. In particular embodiments, such adjuncts include DNA, RNA, antibiotics or peptides that exert a bacteriostatic or bacteriocidal effect on at least one bacterium in the vicinity of the bioimplant. In some embodiments, such adjuncts include DNA, RNA or a peptide that interferes with one or more stages of a viral life cycle, thereby exerting antiviral effects on the virus.

In particular embodiments, the bioimplant presents the adjunct molecule on its surface, whereby the presented adjunct molecule provides its tissue healing, remodeling, growth or regrowth activity. In some such embodiments, the thus presented adjunct is a growth factor, which recruits one or more bioimplant recipient molecules or cells to the bioimplant site, e.g. by ligating with such molecules or binding to receptors on such cells. In other such embodiments, the thus presented adjunct exerts its tissue healing, remodeling, growth or regrowth activity by interacting with a receptor on the a bacterial cell surface that is associated with inducing apoptosis or cell lysis in the bacterial cell.

In other particular embodiments, the bioimplant releases the adjunct molecule into the vicinity of the bioimplant by cleaving, e.g. by hydrolysis (whether enzyme mediated or non-enzyme mediated), one or more covalent bonds conjugating the adjunct to the biological tissue. The thus cleaved covalent bonds may be amide, ester, anhydride or urea bonds, depending upon the conjugating agent used to conjugate the adjunct molecule to the biological tissue. In particular embodiments, in which the conjugating agent is a diamine, the covalent bonds are amide bonds, which are cleaved by hydrolysis to form a free amine chain and a carboxyl group.

The bioimplants of the invention are useful in a variety of surgical procedures. In some embodiments, the bioimplants are soft tissues that may be used to augment repair, such as suturing, closure of surgical wounds, or repair or replacement of tendons, ligaments, skin, etc. In some embodiments, the bioimplants are heart valves useful in the alleviation of vascular or arterial valve occlusion (stenosis) or other valve malfunction. In some embodiments, the bioimplants are partially or completely demineralized bone or bone fragments useful in bone repair, bioimplantation (e.g. hip, knee or other joint implantation) or spinal fusion surgery. The person of skill in the art will recognize that other bioimplantation methods are encompassed within the present invention and are well within the skill in the person of skill in the relevant surgical art.

Preparative Methods

The sections below describe in more detail sterilization of biological tissue, conjugation of adjunct molecules to the biological tissue, and optional tissue crosslinking procedures.

Crosslinking Biological Tissue

Bioimplants of the invention comprise biological tissues from natural sources. In the case of complex composites, they also comprise other materials from non-natural sources. In some embodiments, the types of tissue that are used include dermis, pericardium, tendon, ligament, fascia and reconstituted collagen scaffold, as well as bone fragments and demineralized bone. In some embodiments, soft tissues include multiple components, such as living cells and collagen. Collagen is fibrous proteinaceous biopolymer (scaffolding) that forms the matrix that provides structural integrity to soft tissues. Collagen is also the fibrous protein constituent of cartilage and bone. Soft tissues can be decellularized to provide a decellularized scaffolding that is made up primarily of collagen. Mineralized tissue (bone) can be demineralized to provide a collagen scaffold that is optionally decellularized. In any case, collagen and other proteins in soft tissue have numerous functional groups that can be caused to react to form bonds with other functional groups.

Bioimplants comprising naturally occurring biological tissues, such as tissues extracted from a human, porcine, ovine, bovine, caprine, murine, canine, feline or other source, are generally unstable if left in their natural state. Having been extracted from the living environment within the body, such tissues will soon degrade unless stabilized. Microbes that naturally occur within the biological tissues, or which infest the biological tissues after they have been excised, will soon begin to break down the biological tissue as food. Also, naturally occurring antigens on the tissue, especially on the part of the tissue that is exposed to the interstitial fluid surrounding the bioimplant, attract components of the recipient body's immune system, which gradually break down the tissue and eventually give rise to tissue rejection. Also, protein on the surface of the untreated (fresh) biological tissue is easily denatured, which can lead to its gradual erosion within the recipient body. In non-decellularized soft tissue, cells within the tissue may undergo lysis (cell membrane rupture), thereby disturbing the structural integrity of the tissue and potentially exposing various antigens to the bioimplant surface. Thus, it is desirable to sterilize the biological tissue during the course of preparing the bioimplant of the present invention. Such sterilization kills microbes associated with the biological material and in some embodiments masks antigenic sites, provides structural integrity to the bioimplant, and/or retains the bioimplant in its natural shape.

In embodiments of the invention, the bioimplant is an organ or tissue derived in whole or in part from a human or an animal, or which is produced from other organic tissue, and which is to be implanted, either by itself or as part of a bioprosthesis, in a human or in an animal. Thus, bioimplants generally include hearts, heart valves and other heart components, pericardium, vascular grafts, urinary tract and bladder components, tendons, bowel, and soft tissues in general, such as skin, collagen and the like. In particular embodiments, bioimplants include decellularized collagen matrix, purified collagen matrix and purified collagen matrix. In some embodiments, a bioimplant can be a xenograft, an allograft or an autograft. In some embodiments, the bioimplants also include bone tissue, especially bone fragments and demineralized bone tissue. Although the bioimplant will very often be one which is made from natural tissues, including but not limited to bovine, ovine, porcine, caprine, canine, feline and possibly even human tissue, other natural materials, well known to those having ordinary skill in this art, also can be used. Such additional materials include hydrogels (e.g. hyaluronic acid hydrogels), alginates and chitosan.

The term "crosslinking", as used herein, refers to the formation of links of various lengths within the tissue—that is within and/or between the molecules (especially the proteins) of the tissue, such links resulting from bond formation either (a) between two reactive moieties of the tissue, thus forming short covalent links within and between the molecules of the tissue, or (b) between reactive moieties on the tissue and a covalently bound bifunctional crosslinking agent. While crosslinking and "conjugating" are diverse events (the former forming bonds within the biological tissue, the latter forming bonds between the biological tissue and an adjunct molecule), in many instances crosslinking and conjugating may be carried out in the same process step, as discussed in more detail herein.

The term "crosslinking agent" is used herein to describe a bifunctional reagent capable of reacting with two or more functional groups in the biological tissue. A bifunctional reagent is a reagent having at least two functional groups capable of reacting with reactive groups in the biological tissue. Such functional groups include amines, acids hydroxyls and thiols (sulfhydryl groups). Thus, bifunctional reagents include diamines, diacids, or a β-, γ-, δ-, ε-, ζ-, or higher order amino acid, or other bifunctional agents, such as anhydrides (e.g. succinic anhydride). The bifunctional reagents are chosen to react with reactive groups in the biological tissue. Such reactive groups include amines (e.g. N-terminal amines and generally ubiquitous lysine groups), other —$NH_2$ groups (such as those on guaninyl groups of arginine residues), free carboxyl groups (e.g. those at the C-terminus and aspartic and glutamic acid groups), hydroxyl groups (e.g. those found on serine, threonine and tyrosine) and thiols (e.g. those found in cysteine residues). Thus, in some embodiments, the crosslinks comprise covalent bonds, such as amides (formed between bifunctional reagent amines and carboxyl groups in the biological tissue, or between bifunctional reagent acids or anhydrides and protein amines). In some embodiments, the crosslinks comprise esters, such as those formed between carboxyl groups on the bifunctional reagent and hydroxyl groups in the protein or those formed between hydroxyl groups on the bifunctional reagent and carboxyl groups in the protein. In still further embodiments, the crosslinks comprise disulfide bonds, e.g. between thiols on the bifunctional reagent and cysteine in the protein. Of the types of bonds that can be formed, amides are particularly advantageous as they can be easily formed using methods described herein using a coupling agent, optionally in conjunction with a coupling enhancer, as described in more detail herein.

In some embodiments, the crosslinking agent is a straight chain or a branched compound having from 4 to 12 carbon atoms. In some embodiments, the crosslinking agent is a carbocyclic compound in which the reactive functional groups are on the carbocyclic ring or are attached to the carbocyclic ring by an intervening carbon chain. In some embodiments, the reactive functional groups can include amines, hydroxyl groups, carboxylic acids, anhydrides, acid chlorides, thiols, etc. In particular embodiments, the crosslinking agent is a $C_4$-$C_{12}$ alkanediamine, alkenediamine, alkynediaminealkane, aminoalkanoic acid, aminoalkenoic acid or aminoalkynoic acid. In specific embodiments, the crosslinking agent is 1,6-diaminohexane, 1,7-diaminoheptane, succinic acid ($C_4$), glutaric acid ($C_5$), adipic acid ($C_6$) or pimelic acid ($C_7$), or one of the anhydrides selected from: succinic, glutaric, adipic and pimelic anhydride. In other particular embodiments, the crosslinking agent is 2,4,6-triaminobenzene, 1,4-diaminobenzene, o-phthalic acid, p-phthalic acid, 4-aminobenzoic acid and phthalic anhydride. In some embodiments, a di- or triamino crosslinking agent that has a molecular weight of about 190 or less, and about 150 or less, is employed so as to assure adequate penetration into the fresh tissue. In particular embodiments, the crosslinking agent is a straight chain from 6 to 8 carbon atoms in length with one reactive amine located at each end. Although the crosslinking agent may have optional substitutions along its length, in specific embodiments, it is a hydrocarbon that is substituted only with the reactive amines, e.g. a straight chain alkane having amines at each extremity. Exemplary crosslinking agents are 1,6-hexanediamine and 1,7-heptanediamine.

The terms "coupling agent" and "coupling enhancer," as used herein, refer to reagents that respectively promote and enhance the formation of bonds, especially amide bonds, between proteins within the bioimplant tissue or between functional groups (e.g. amines or carboxyls) on the proteins and the crosslinking agent. These bonds may be formed between a reactive amine and a reactive carboxyl (COOH or COO—) on the tissue (thus linking two such closely located reactive groups), or between a reactive amine or carboxyl on a crosslinking agent and a reactive carboxyl or amine on or within the tissue. Those of skill in the peptide synthesis and related art will be familiar with such reagents, e.g. carbodiimides and succinimides, especially water-soluble varieties thereof.

In some embodiments, the crosslinking reaction is facilitated by use of a coupling agent. In some more particular embodiments, the coupling agent is 1-ethyl-3(3-dimethyl aminopropyl)carbodiimide hydrochloride (EDC), although other suitable coupling agents such as N-hydroxysuccinimide (NHS) can also be used. In particular embodiments, the coupling agent is used in conjunction with a coupling enhancer, such N-hydroxysulfosuccinimide (sulfo-NHS) although other suitable coupling enhancers, such as 1-hydroxy-benzotriazole (HOBt) and dimethylaminopyridine (DMAP), can also be used. The concentration of the coupling agent and of the coupling enhancer can vary. However, appropriate concentrations are readily determinable by those of skill in the art. In some embodiments, the coupling agent is used in a concentration between about 10 mM and 500 mM, at a concentration of 100 mM or less, especially at a concentration of between about 20 mM and 50 mM. In some embodiments, the coupling enhancer is employed at a concentration of between 0.5 mM and about 50 mM, especially at a concentration of about 10 mM or less.

In some embodiments of the present invention, the crosslinking agents, the coupling agent and the coupling enhancer as well as their reaction products are water soluble. In particular embodiments, the selected crosslinking agent, coupling agent and coupling enhancer to optimize crosslinking of the tissue, while minimizing the risks of damage to the biological tissue during the crosslinking process, and of toxicity, inflammation, calcification, etc, after implantation. In specific embodiments, all solutions used for crosslinking are filtered before use, e.g. through 0.45 µm or less filters to remove microbial contaminants, and thereby reduce the risk of contaminating the tissue during crosslinking and/or sterilization.

Reaction conditions for the crosslinking of the biological tissue may vary, depending on the crosslinking, coupling and enhancing agents employed. In general, the crosslinking process is carried out in an aqueous buffer selected from among those well known to those of ordinary skill in this art as to provide the most efficacious crosslinking reaction, while minimizing risks of calcification. Examples of suitable buffers include, but are not limited to, N-2-hydroxyethylpiperazine-N'-ethanesulfonic acid (HEPES) and 3-(N-morpholino) propanesulfonic acid (MOPS), and the like.

The pH and concentration of the buffered solution can vary, again depending upon the crosslinking, coupling and enhancing agents employed. The buffer concentration and pH are chosen to provide the most effective crosslinking reaction while being the least harmful to the biological tissue. For example, with EDC as the coupling agent and sulfo-NHS as the coupling enhancer, the pH of the treatment solution is maintained at between about 6.0 to about 7.4. The reaction temperature may be between about 40° C. and 0° C.; e.g. between about 21° C. and 25° C. Acceptable pH buffers for use in embodiments of the invention include the commonly known HEPES, TRIS and MOPS pH buffers.

Generally, a fresh or adjunct conjugated biological tissue to be crosslinked according to the present invention is kept on ice until it can be rinsed several times in ice-cold 0.85% saline or some other suitable solution. In general, such washing or rinsing is carried out immediately after fresh biological tissue has been excised from the donor animal, or within 48 hours thereafter. In the case of adjunct conjugated biological tissue, the rinsing step may be skipped if the tissue is to be immediately crosslinked after the adjunct has been conjugated to the biological tissue. If additional storage time is needed, the rinsed tissue can be stored for not longer than for 24 hours, in an appropriate buffer at a low temperature, such as about 4° C.

In some embodiments, the concentration of the diamine crosslinking agent is between about 80 and about 135 millimolar, between about 90 and 130 millimolar, between about 95 and 125 millimolar, or between about 100 and 125 millimolar. In particular embodiments, the diamine crosslinking agent has a carbon chain length not greater than 12 carbon atoms, e.g. between 4 and 8 carbon atoms. In specific embodiments, the crosslinking agent is a straight chain alkane having amine groups at its respective ends, especially 1,6-hexanediamine. Treatment of the biological tissue is carried out by contacting the tissue with a solution, especially an aqueous solution, containing the coupling agent, the coupling enhancer and the crosslinking diamine. The concentrations of the coupling agent, EDC, and the coupling enhancer, Sulfo-NHS, are as previously discussed, e.g. between about 10 mM and about 100 mM of EDC and between about 0.5 mM and about 10 mM of sulfo-NHS.

Conjugation of Adjunct Molecules to Biological Tissue

As discussed above, bioimplants of the invention are made from naturally occurring biological tissue, such as dermis, pericardium, tendon, ligament, fascia, and collagen, such as purified collagen, reconstituted collagen and solubilized collagen, as well as bone fragments and demineralized bone. All tissues contemplated within the scope of the invention have therein one or more proteins, such as collagen. Non-decellularized tissues also comprise other components, such as living cells, which have various cell surface proteins, such as receptors, ion channels and other proteins that have numerous functional groups that can be caused to react with various reagents to form covalent bonds.

Various adjunct molecules also have one or more functional groups that can be caused to react with a reagent to form covalent bonds. Exemplary adjunct molecules include proteins, small peptides, ribonucleic acids, deoxyribonucleic acids, polysaccharide, glycosaminoglycan (GAG)s and antibiotics. Each of these classes of adjunct molecules possesses members having at least one reactive group capable of forming an intermolecular covalent attachment (conjugation) between the adjunct molecules and proteins in the biological tissue. Such reactive groups include carboxyl groups, sulfonates, amines, ureas, carbamates, guanidyls, thiols (sulfhydryls) and hydroxyls. Of these reactive groups, the most favorable for preparing bioimplants of the invention are considered to be carboxyl groups and amine groups, as these may be used to form in vivo labile amide groups with carboxyl on protein or bifunctional crosslinking agent.

It will be understood that a functional group of a particular type can be transformed into a different type by methods known in the art. For example, an amine group can be converted to a carboxyl group by reacting the amine with, for example, a diacid or diacid anhydride. Reaction of the amine with one carboxyl group of the diacid, or ring opening of the anhydride of the diacid anhydride, results in an amide bond being formed between the reagent molecule and the amine as well as a free acid group that may be caused to react with another reagent. As another example, a cysteine group may be transformed into a carboxylic acid reactive site by coupling a thiolalkanoic acid to the cysteine group, thereby forming a disulfide bridge between the adjunct molecule and the reagent, while at the same time providing an acid group as a functional group on the adjunct molecule. In some embodiments, an adjunct molecule may have a functional group that is an ester of an acid that can be liberated by hydrolysis of the ester bond to produce a free acid, which can then be conjugated through an amine conjugating agent. This approach is especially useful where the free acid represents the active metabolite in vivo. Thus, as used herein, the term "adjunct molecule" includes such derivatized molecules, especially where release of the adjunct molecule post implantation is effected by cleavage of the bonds formed by the reagents and the adjuncts in vivo, thereby releasing an active molecule.

In general, conjugation entails contacting an adjunct with at least one conjugation reagent. Such conjugation reagents include one or more of the following: crosslinking agents, coupling agents and/or coupling enhancers. In some embodiments, the conjugation reagent includes crosslinking agent only. In other, preferred, embodiments the conjugation reagent includes coupling agent (such as EDC). In more preferred embodiments, the conjugation reagent includes coupling agent (such as EDC) and a coupling enhancer (such as NHS or Sulfo-NHS). In some embodiments, the conjugation reagent includes coupling agent and coupling enhancer but no crosslinking agent. In other embodiments, the conjugation reagent includes coupling agent, coupling enhancer and crosslinking agent. In some embodiments, the crosslinking agent, coupling agent and coupling enhancer are the same as those described above with respect to crosslinking of biological tissue.

In some preferred embodiments, the conjugation reagent comprises a coupling agent and optionally a coupling enhancer. In some particularly preferred embodiments, the coupling agent is a carbodiimide, such as EDC. In some particularly preferred embodiments, the coupling enhancer is NHS or Sulfo-NHS. Coupling agents and coupling enhancers are described in more detail above. Use of a coupling agents alone or in combination with coupling enhancers result in direct amide bonds between the adjunct molecules and the proteins in the biological tissue.

The person skilled in the art will recognize that the coupling reagent and the coupling enhancer disclosed herein for coupling the adjunct to the biological tissue are, in some embodiments, the same as the sterilizing agent and the sterilizing enhancer, respectively, as disclosed above. One of skill in the art will recognize that a preferred embodiment entails sterilization and conjugation in the same step, using a sterilizing agent as a coupling agent and optionally a sterilizing enhancer as a coupling enhancer. In some preferred embodiments, then, coupling is also carried out in the presence of a penetration enhancer, as disclosed above. In some preferred embodiments, the tissue and the adjunct are combined and then contacted with a sterilization solution comprising sterilizing agent and optionally sterilizing enhancer and/or penetration enhancer. In particularly preferred embodiments, the tissue and adjunct are combined, frozen, lyophilized and then contacted with said sterilization solution. In other preferred embodiments, the tissue is contacted with a sterilization solution comprising adjunct molecule and sterilizing agent and optionally a sterilizing enhancer and/or penetration enhancer. In particularly preferred embodiments, the tissue is first frozen and lyophilized and then contacted with a sterilization solution comprising adjunct molecule and sterilizing agent and optionally a sterilizing enhancer and/or penetration enhancer.

In some embodiments, a crosslinking agent is used. In such cases, at least one functional group on the crosslinking agent is capable of forming a covalent bond with a functional group on the adjunct molecule. At least one other functional group is capable of forming a covalent bond with a functional group on the protein of the biological tissue. In such cases, the active group on the adjunct molecule is one that readily forms a covalent bond with a functional group on the crosslinking agent. Exemplary active groups that may be found on adjunct molecules include carboxyl groups, sulfonates, amines, guanines, ureas, carbamates, amides, imides and thiols (e.g. cysteine groups on proteins, such as growth factor proteins). Especially suitable active groups include carboxyl groups and amines.

In some embodiments, suitable crosslinking agent functional groups include functional groups that form amide or ester bonds with at least one carboxyl group on the adjunct. Such functional groups include amines and hydroxyls. In some embodiments, suitable conjugation agent functional groups include functional groups that form amide or ester bonds with at least one amine or hydroxyl on the adjunct molecule. Such functional groups include carboxyl groups and acid anhydrides.

Some crosslinking agents that may be used to conjugate an adjunct to a protein in a biological tissue include the homobifunctional, water soluble reagents: bis-(sulfosuccinimidyl) suberate, disulfosuccinimidyl tartrate, and ethylene glycol-bis-(sulfosuccinimidyl succinate). Other conjugating agents include the heterobifunctional, water soluble reagents: N-sulfosuccinimidyl(4-iodoacetyl)aminobenzoate, sulfosuccinimidyl-4-(N-maleimidomethyl)cyclohexane-1-carboxylate, sulfosuccinimidyl-4-(p-maleimidophenyl)butyrate, 3-Maleimidobenzoyl-N-hydroxysulfosuccinimide ester. While water soluble reagents are considered to be superior to non-water soluble reagents, it is also possible to use non-water soluble bifunctional crosslinking agents, such as bis-(succinimidyl)suberate, disuccinimidyl tartrate, and ethylene glycol bis-(succinimidyl succinate). Other crosslinking agents that may be mentioned include: dimethyl-3,3'-dithiobispropionimidate, dimethyl-4,4'-dithiobisbutyrimidate, and dimethyl-6-6'-dithiobiscaproimidate.

Some especially suitable bifunctional crosslinking agents include diamines, diacids and amino acids, and in particular diamines, diacids and amino acids having from 4 to 12 carbons between the functional groups. Where diamines, diacids or amino acids are used as conjugating agents, it is advantageous to use a coupling agent (such as a carbodiimide or a cyclic imide) and/or a coupling enhancer (such as a cyclic imide, HOBt or DMAP), as described in more detail herein.

Conjugating Proteins to Biological Tissue

The proteins that are considered within the scope of the present invention include growth factors and proteoglycans. The proteins may be recombinant proteins or proteins that have been isolated from the tissues in which they are naturally expressed. The growth factors that are considered within the scope of the present invention include transforming growth factor-β, platelet derived growth factor, fibroblast growth factor, insulin-like growth factors, cartilage derived growth factors, and bone growth factors, such as the bone morphogenic proteins. Some bone morphogenic proteins that are considered within the scope of the present invention include bone morphogenic protein-1, bone morphogenic protein-2, bone morphogenic protein-4 and bone morphogenic protein-7. Exemplary proteoglycans within the scope of the present invention include glycosaminoglycan. Each of the aforementioned proteins has within its primary structure one or more amino acids having N-terminal, C-terminal and/or side chain functional groups that may be caused to react with coupling reagents to effect an intermolecular link between the adjunct protein and a protein in the biological tissue. In particular embodiments, proteins within the scope of the invention have at least one side chain carboxyl group (e.g. aspartic acid or glutamic acid side chains) or amine (e.g. arginine or lysine side chain) that can be caused to react with a reagent to form intermolecular links between the adjunct protein and proteins belonging to the biological protein. In some preferred embodiments, the conjugation reagent comprises a coupling agent and optionally a coupling enhancer and/or a penetration enhancer but no crosslinking agent. This results in direct bonds between the adjunct protein and the biological tissue. In other embodiments, the conjugation reagent comprises a diamine. In other embodiments, the conjugation reagent comprises a diamine and is coupled to protein in the presence of a coupling agent, such as EDC, optionally in the presence of a coupling enhancer, such as sulfo-NHS or NHS. In some such embodiments, the conjugating reagent is an amino acid, such as a β-amino acid, a γ-amino acid, a δ-amino acid, an ε-amino acid, a ζ-amino acid or higher order amino acid, such as β-aminoacetic acid, γ-aminobutyric acid, δ-aminovaleric acid or ζ-aminocaproic acid. Contacting the biological tissue with the adjunct protein, the amino acid conjugating agent and a coupling agent, such as EDC, optionally in the presence of a coupling enhancer, such as NHS, results in conjugation of the adjunct protein to proteins in the biological tissue through amide bonds formed between the adjunct protein and the amino acid and between the amino acid and proteins in the biological tissue.

Conjugating Small Peptides to Biological Tissues

The present invention also provides methods of making bioimplants in which small peptides are conjugated to biological tissue. In some embodiments, the small peptide is a binding domain of a growth protein or a portion of a proteoglycan having the desired property promoting tissue healing, remodeling, growth or regrowth. Other small peptides having the desired property promoting tissue healing, remodeling, growth or regrowth are known and are contemplated within the scope of this invention. In general, conjugation of small peptides to biological tissue is entirely analogous to conjugation of proteins to biological tissue. In some particular embodiments, the peptide has a free carboxyl group (e.g. a C-terminal carboxyl group or a side chain carboxyl group, such as an aspartic acid or glutamic acid side chain), a free amino group (such as an N-terminal $NH_2$ or a lysine side chain amine), a cysteine side chain or other reactive functional group amenable to formation of a conjugation between the peptide and one or more proteins in the biological tissue. In some exemplary embodiments, the adjunct molecule is a peptide having at least one free amine group (e.g. an N-terminal $NH_2$ group an arginine guanidinyl group or a lysine side chain $NH_2$ group), which is contacted with a fresh or crosslinked biological tissue in the presence of a β-amino acid, a γ-amino acid, a δ-amino acid, an ε-amino acid, a ζ-amino acid or higher order amino acid, such as β-aminoacetic acid, γ-aminobutyric acid, δ-aminovaleric acid or ζ-aminocaproic acid, in the presence of a coupling agent, such as EDC, and optionally in the presence of a coupling enhancer, such as NHS. In other exemplary embodiments, the peptide has at least one free carboxyl group (e.g. the C-terminal or an aspartic or glutamic acid side chain carboxyl) and the conjugating reagent is a diamine (e.g. 1,5-pentanediamine, 1,6-hexanediamine or 1,7-heptanediamine). In such cases, the biological tissue is contacted with the adjunct peptide, diamine and a coupling enhancer, such as EDC, optionally further in the presence of a coupling enhancer, such as sulfo-NHS or NHS.

Suitable amine-bearing adjunct include proteins and peptides, as well as certain antibiotics. Particular proteins that may be mentioned as having available amine groups are transforming growth factor beta (TGF-β), platelet derived growth factor (PDGF), insulin-like growth factors (IGFs), cartilage derived growth factors (CDGF), fibroblast growth factor (FGF) and the bone growth factors (BGFs), such as the bone morphogenic proteins (BMPs), particularly BMP-2, BMP-4 and BMP-7, as well as osteogenic protein-1.

Particular amine-bearing peptides within the scope of the present invention include the magainins (e.g. magainin I and magainin II), which have several lysine residues in their peptide chains.

In some preferred embodiments, the conjugation reagent comprises a coupling agent and optionally a coupling enhancer and/or a penetration enhancer but no crosslinking agent. This results in direct bonds between the adjunct peptide and the biological tissue. In other embodiments, the conjugation reagent comprises a diamine. This results in indirect covalent attachment between the peptide and the biological tissue.

Conjugating Nucleic Acids to Biological Tissue

In some embodiments of the invention, the adjunct molecule is a nucleic acid, such as a ribonucleic acid, a deoxyribonucleic acid or a nucleic acid mimetic. Such nucleic acids may be conjugated to a protein through known methods, such as by phosphoramidite method using a reagent having a phosphoramidite functionality at one end and a protein-reactive functionality, such as an amine, at the other end. The phosphoramidite is reacted with a free hydroxyl group (5'-OH, 3'-OH, etc.) of the nucleic acid, e.g. in the presence of a catalyst such as tetrazole or dicyanotimidazole, to form a phosphite intermediate, which is then oxidized e.g. with oxygen, sulfur or an oxygen or sulfur reagent, such as hydrogen peroxide or phenylacetyldisulfide, to form a phosphate bond between the reagent molecule and the nucleic acid. This derivative may then be coupled to a protein. For example, if an aminoalkyl phosphoramidite is used, the amino group is free to react with reactive carboxyl groups on the protein surface after the phosphate bond is formed. Coupling of the amine group to carboxyl groups can be effected in the presence of a coupling agent and optionally a coupling enhancer as described in the crosslinking section above. In particular embodiments, the coupling agent is a carbodiimide, such as EDC, and the coupling enhancer is sulfo-NHS or NHS.

Conjugating Antibiotics to Biological Tissues

The present invention also provides methods of providing adjunct conjugated bioimplants in which the conjugated adjunct is an antibiotic. As in the case of proteins, suitable antibiotics are those having a free amine, carboxyl or other functional group, as well as those that can be considered ester or amide pro-drugs of free carboxyl and/or free amine active metabolites. The latter must be de-esterified or de-amidated prior to conjugation. Suitable amine functional groups have at least one —$NH_2$ or —$NH_3^+$ group available for formation of an amide or sulfonamide bond with a suitable functional group on the conjugating agent. The person skilled in the art will recognize that a variety of functional groups have such —$NH_2$ and/or —$NH_3^+$ functional groups, including: amines (—$NH_2$ or —$NH_3^+$), amides (—$CONH_2$), sulfonamides (—$SO_2NH_2$), urea (—$NHCONH_2$), thiourea (—NHC-SNH$_2$), carbamates (—$OCONH_2$), guanidines (—N—(C=NH)—$NH_2$), etc. In some exemplary embodiments, the adjunct molecule is an antibiotic having at least one free amine group (e.g. an N-terminal $NH_2$ group or a lysine side chain $NH_2$ group), which is contacted with a fresh or crosslinked biological tissue in the presence of a β-amino acid, a γ-amino acid, a δ-amino acid, an ε-amino acid, a ζ-amino acid or higher order amino acid, such as β-aminoacetic acid, γ-aminobutyric acid, δ-aminovaleric acid or ζ-aminocaproic acid, in the presence of a coupling agent, such as EDC, and optionally in the presence of a coupling enhancer, such as NHS. In other exemplary embodiments, the antibiotic has at least one free carboxyl group (e.g. the C-terminal or an aspartic or glutamic acid side chain carboxyl) or sulfite (—$SO_3H$) group and the conjugating reagent is a diamine (e.g. 1,5-pentanediamine, 1,6-hexanediamine or 1,7-heptanediamine). In such cases, the biological tissue is contacted with the adjunct antibiotic, diamine and a coupling enhancer, such as EDC, optionally further in the presence of a coupling enhancer, such as NHS. In still further embodiments, the antibiotic has at least one free —OH group capable of forming an ester or phosphodiester bond with a suitable crosslinking reagent, such as succinic acid, succinic acid anhydride or 5-aminopentylsulfon-1-ic acid. In some preferred embodiments, the conjugation reagent comprises coupling agent and optionally coupling enhancer and/or penetration enhancer, but no crosslinking agent. This results in direct covalent bonds between the adjunct antibiotic and the biological tissue.

Aminoglycosides having at least one amine group (i.e. —$NH_2$ or —$NH_3^+$) available for forming an amide or sulfonamide bond include: amikacin, apramycin, arbekacin, bambermycins, butirosin, dibekacin, dihydrostreptomycin, fortimicins, gentamicin, isepamicin, kanamycin (A, B or C), micronomicin, neomycin (A, B or C), netilmicin, paromomycin, ribostamycin, sisomicin, streptomycin, tobramycin and trospectomycin. In some preferred embodiments, the conjugation reagent comprises coupling agent and optionally coupling enhancer and/or penetration enhancer, but no crosslinking agent. This results in direct covalent bonds between the adjunct aminoglycoside and the biological tissue.

B-Lactam antibiotics having at least one amine group (i.e. —$NH_2$ or —$NH_3^+$) available for forming an amide or sulfonamide bond include members of the antibiotic families: cephalosporins, cephamycins, monobactams, penicillins and ritapenem. In some preferred embodiments, the conjugation reagent comprises coupling agent and optionally coupling enhancer and/or penetration enhancer, but no crosslinking agent. This results in direct covalent bonds between the adjunct β-lactam and the biological tissue.

Cephalosporins having at least one amine group (i.e. —$NH_2$ or —$NH_3^+$) available for forming an amide or sulfonamide bond include: cefaclor, cefadroxil, cefatrizine, cefcapene pivoxil, cefclidin, cefdinir, cefditoren, cefepime, cefetamet, cefixime, cefmenoxime, cefodizime, ceforanide, cefotaxime, cefotiam, cefozopran, cefpirome, cefpodoxime proxetil, cefprozil, cefroxadine, cefsoludin, ceftazidime, cefteram, ceftibuten, ceftiofur, ceftriaxone, cefuroxime, cefuzonam, cephalexin, cephaloglycin, cephalosporin C, cephamycins, cephradine and pivcefalexin. In some preferred embodiments, the conjugation reagent comprises coupling agent and optionally coupling enhancer and/or penetration enhancer, but no crosslinking agent. This results in direct covalent bonds between the adjunct cephalosporin and the biological tissue.

Cephamycins having at least one amine group (i.e. —$NH_2$ or —$NH_3^+$) available for forming an amide or sulfonamide bond include: cefotetan and cefoxitin. In some preferred embodiments, the conjugation reagent comprises coupling agent and optionally coupling enhancer and/or penetration enhancer, but no crosslinking agent. This results in direct covalent bonds between the adjunct cephamycin and the biological tissue.

Monobactams having at least one amine group (i.e. —$NH_2$ or —$NH_3^+$) available for forming an amide or sulfonamide bond include: aztreonam, carumonam and tigemonam. In some preferred embodiments, the conjugation reagent comprises coupling agent and optionally coupling enhancer and/or penetration enhancer, but no crosslinking agent. This results in direct covalent bonds between the adjunct monobactam and the biological tissue.

Penicillins having at least one amine group (i.e. —$NH_2$ or —$NH_3^+$) available for forming an amide or sulfonamide bond include: amoxicillin, ampicillin, aspoxicillin, bacampicillin, cyclacillin, epicillin, lenampicillin, penicillin N, pivampicillin, sultamicillin and talampicillin. In some preferred embodiments, the conjugation reagent comprises coupling agent and optionally coupling enhancer and/or penetration enhancer, but no crosslinking agent. This results in direct covalent bonds between the adjunct penicillin and the biological tissue.

Macrolides having at least one amine group (i.e. —$NH_2$ or —$NH_3^+$) available for forming an amide or sulfonamide bond include primycin. In some preferred embodiments, the conjugation reagent comprises coupling agent and optionally coupling enhancer and/or penetration enhancer, but no crosslinking agent. This results in direct covalent bonds between the adjunct macrolide and the biological tissue.

Polypeptides having at least one amine group (i.e. —$NH_2$ or —$NH_3^+$) available for forming an amide or sulfonamide bond include: bacitracin, capreomycin, colistin, enduracidin, enviomycin, polymyxin, ristocetin, teicoplanin, thiostrepton, tuberactinomycin, tyrocidine and vancomycin. In some preferred embodiments, the conjugation reagent comprises coupling agent and optionally coupling enhancer and/or penetration enhancer, but no crosslinking agent. This results in direct covalent bonds between the adjunct polypeptide and the biological tissue.

Tetracyclines having at least one amine group (i.e. —NH$_2$ or —NH$_3^+$) available for forming an amide or sulfonamide bond include: chlortetracycline, demeclocycline, doxycycline, guamecycline, lymecycline, meclocycline, methacycline, minocycline, oxytetracycline, sancycline and tetracycline. In some preferred embodiments, the conjugation reagent comprises coupling agent and optionally coupling enhancer and/or penetration enhancer, but no crosslinking agent. This results in direct covalent bonds between the adjunct tetracycline and the biological tissue.

2,4-Diaminopyrimidines having at least one amine group (i.e. —NH$_2$ or —NH$_3^+$) available for forming an amide or sulfonamide bond include brodimoprim. In some preferred embodiments, the conjugation reagent comprises coupling agent and optionally coupling enhancer and/or penetration enhancer, but no crosslinking agent. This results in direct covalent bonds between the adjunct 2,4-diaminopyrimidine and the biological tissue.

Quinolone and quinolone analog adjuncts having at least one amine group (i.e. —NH$_2$ or —NH$_3^+$) available for forming an amide or sulfonamide bond include: ciprofloxacin, clinafloxacin, enoxacin, grepafloxacin, lomefloxacin, norfloxacin, pipemidic acid, sparfloxacin, temafloxacin, tosufloxacin and trovafloxacin. In some preferred embodiments, the conjugation reagent comprises coupling agent and optionally coupling enhancer and/or penetration enhancer, but no crosslinking agent. This results in direct covalent bonds between the adjunct quinolone or quinolone analog and the biological tissue.

Sulfonamides having at least one amine group (i.e. —NH$_2$ or —NH$_3^+$) available for forming an amide or sulfonamide bond include: acetylsulfamethoxypyrazine, benzylsulfamide, chloramine-B, chloramine-T, N$^4$-β-D-glucosylsulfanilamide, mafenide, 4'-(methylsulfamoyl)sulfanilanilide, noprylsulfamide, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, N$^4$-sulfanilylsulfanilamide, sulfanilylurea, N-sulfanilyl-3,4-xylamide, sulfaperine, sulfaphenazole, sulfaproxyline, sulfapyrazine, sulfapyridine, sulfaquinoxaline, sulfasomizole, sulfasymazine, sulfathiazole, sulfathiourea, sulfatolamide, sulfazamet, sulfisomidine and sulfisoxazole. In some preferred embodiments, the conjugation reagent comprises coupling agent and optionally coupling enhancer and/or penetration enhancer, but no crosslinking agent. This results in direct covalent bonds between the adjunct sulfonamide and the biological tissue.

Sulfones having at least one amine group (i.e. —NH$_2$ or —NH$_3^+$) available for forming an amide or sulfonamide bond include: acediasulfone, acetosulfone sodium, dapsone, succisulfone, sulfanilic acid, 2-p-sulfanilylanilinoethanol, p-sulfanilylbenylamine and thiazolsulfone. In some preferred embodiments, the conjugation reagent comprises coupling agent and optionally coupling enhancer and/or penetration enhancer, but no crosslinking agent. This results in direct covalent bonds between the adjunct sulfone and the biological tissue.

Aminoglycosides having at least one acid group (i.e. COOH, COO$^-$, SO$_3$H, SO$_3^-$) available for forming an amide (or in the case of SO$_3$H or SO$_3^-$, sulfonamide) bond include the bambermycins.

B-Lactams having at least one acid group (i.e. COOH, COO$^-$, SO$_3$H, SO$_3^-$) available for forming an amide (or in the case of SO$_3$H or SO$_3^-$, sulfonamide) bond include members of the β-lactam families: carbacephems, carbapenems, cephalosporins, cephamycins, monobactams, oxacephems, penicillins, clavulanic acid and ritapenem. In some preferred embodiments, the conjugation reagent comprises coupling agent and optionally coupling enhancer and/or penetration enhancer, but no crosslinking agent. This results in direct covalent bonds between the adjunct β-lactam and the biological tissue.

Carbapenems having at least one acid group (i.e. COOH, COO$^-$, SO$_3$H, SO$_3^-$) available for forming an amide (or in the case of SO$_3$H or SO$_3^-$, sulfonamide) bond include loracarbef. In some preferred embodiments, the conjugation reagent comprises coupling agent and optionally coupling enhancer and/or penetration enhancer, but no crosslinking agent. This results in direct covalent bonds between the adjunct carbapenem and the biological tissue.

Carbapenems having at least one acid group (i.e. COOH, COO$^-$, SO$_3$H, SO$_3^-$) available for forming an amide (or in the case of SO$_3$H or SO$_3^-$, sulfonamide) bond include: biapenem, imipenem, meropenem and panipenem. In some preferred embodiments, the conjugation reagent comprises coupling agent and optionally coupling enhancer and/or penetration enhancer, but no crosslinking agent. This results in direct covalent bonds between the adjunct carbapenem and the biological tissue.

Cephalosporins having at least one acid group (i.e. COOH, COO$^-$, SO$_3$H, SO$_3^-$) available for forming an amide (or in the case of SO$_3$H or SO$_3^-$, sulfonamide) bond include: cefaclor, cefadroxil, cefamandole, cefatrizine, cefazedone, cefazolin, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefprozil, cefroxadine, cefsoludin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephamycins, cephapirin sodium, cephradine and pivcefalexin. In some preferred embodiments, the conjugation reagent comprises coupling agent and optionally coupling enhancer and/or penetration enhancer, but no crosslinking agent. This results in direct covalent bonds between the adjunct cephalosporin and the biological tissue.

Cephamycins having at least one acid group (i.e. COOH, COO$^-$, SO$_3$H, SO$_3^-$) available for forming an amide (or in the case of SO$_3$H or SO$_3^-$, sulfonamide) bond include: cefbuperazone, cefmetazole, cefminox, cefotetan and cefoxitin. In some preferred embodiments, the conjugation reagent comprises coupling agent and optionally coupling enhancer and/or penetration enhancer, but no crosslinking agent. This results in direct covalent bonds between the adjunct cephamycin and the biological tissue.

Monobactams having at least one acid group (i.e. COOH, COO$^-$, SO$_3$H, SO$_3^-$) available for forming an amide (or in the case of SO$_3$H or SO$_3^-$, sulfonamide) bonds include: carumonam and tigemonam. In some preferred embodiments, the conjugation reagent comprises coupling agent and optionally coupling enhancer and/or penetration enhancer, but no crosslinking agent. This results in direct covalent bonds between the adjunct monobactam and the biological tissue.

Oxacephems having at least one acid group (i.e. COOH, COO$^-$, SO$_3$H, SO$_3^-$) available for forming an amide (or in the case of SO$_3$H or SO$_3^-$, sulfonamide) bond include: flomoxef and moxalactam. In some preferred embodiments, the conjugation reagent comprises coupling agent and optionally coupling enhancer and/or penetration enhancer, but no crosslinking agent. This results in direct covalent bonds between the adjunct oxacephem and the biological tissue.

Penicillins having at least one acid group (i.e. COOH, COO⁻, SO$_3$H, SO$_3^-$) available for forming an amide (or in the case of SO$_3$H or SO$_3^-$, sulfonamide) bond include: amdinocillin, amoxicillin, ampicillin, apalcillin, aspoxicillin, azidocillin, azlocillin, benzylpenicillinic acid, carbenicillin, caridacillin, clometocillin, cloxacillin, cyclacillin, dicloxacillin, epicillin, fenbenicillin, floxacillin, hetacillin, metampicillin, methicillin, mezlocillin, nafcillin, oxacillin, penamecillin, penethamate, penicillin G, penicillin N, penicillin O, penicillin V, penimepicycline, phenethicillin, piperacillin, propicillin, quinacillin, sulbenicillin, temocillin and ticarcillin. In some preferred embodiments, the conjugation reagent comprises coupling agent and optionally coupling enhancer and/or penetration enhancer, but no crosslinking agent. This results in direct covalent bonds between the adjunct penicillin and the biological tissue.

Polypeptides having at least one acid group (i.e. COOH, COO⁻, SO$_3$H, SO$_3^-$) available for forming an amide (or in the case of SO$_3$H or SO$_3^-$, sulfonamide) bond include: amphomycin, bacitracin, teicoplanin, tyrocidine and vancomycin. In some preferred embodiments, the conjugation reagent comprises coupling agent and optionally coupling enhancer and/or penetration enhancer, but no crosslinking agent. This results in direct covalent bonds between the adjunct polypeptide and the biological tissue.

Tetracyclines having at least one acid group (i.e. COOH, COO⁻, SO$_3$H, SO$_3^-$) available for forming an amide (or in the case of SO$_3$H or SO$_3^-$, sulfonamide) bond include: apicycline, lymecycline and penimepicycline. In some preferred embodiments, the conjugation reagent comprises coupling agent and optionally coupling enhancer and/or penetration enhancer, but no crosslinking agent. This results in direct covalent bonds between the adjunct tetracycline and the biological tissue.

Quinolone and quinolone analog adjuncts having at least one acid group (i.e. COOH, COO⁻, SO$_3$H, SO$_3^-$) available for forming an amide (or in the case of SO$_3$H or SO$_3^-$, sulfonamide) bond include: cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin and trovafloxacin. In some preferred embodiments, the conjugation reagent comprises coupling agent and optionally coupling enhancer and/or penetration enhancer, but no crosslinking agent. This results in direct covalent bonds between the adjunct quinolone or quinolone analog and the biological tissue.

Sulfonamides having at least one acid group (i.e. COOH, COO⁻, SO$_3$H, SO$_3^-$) available for forming an amide (or in the case of SO$_3$H or SO$_3^-$, sulfonamide) bond include: phthalylsulfacetamide, phthalylsulfathiazole, salazosulfadimidine, succinylsulfathiazole, sulfaloxic acid and 4-sulfanilamidosalicylic acid. In some preferred embodiments, the conjugation reagent comprises coupling agent and optionally coupling enhancer and/or penetration enhancer, but no crosslinking agent. This results in direct covalent bonds between the adjunct sulfonamide and the biological tissue.

Sulfones having at least one acid group (i.e. COOH, COO⁻, SO$_3$H, SO$_3^-$) available for forming an amide (or in the case of SO$_3$H or SO$_3^-$, sulfonamide) bond include: acediasulfone, solasulfone, succisulfone and sulfanilic acid. In some preferred embodiments, the conjugation reagent comprises coupling agent and optionally coupling enhancer and/or penetration enhancer, but no crosslinking agent. This results in direct covalent bonds between the adjunct sulfone and the biological tissue.

Aminoglycosides having at least one hydroxyl group (—OH) capable of forming an ester bond or a phosphodiester bond include spectinomycin. In some preferred embodiments, the conjugation reagent comprises coupling agent and optionally coupling enhancer and/or penetration enhancer, but no crosslinking agent. This results in direct covalent bonds between the adjunct aminoglycoside and the biological tissue.

Lincosamides having at least one hydroxyl group (—OH) capable of forming an ester bond or a phosphodiester bond include clindamycin and lincomycin. In some preferred embodiments, the conjugation reagent comprises coupling agent and optionally coupling enhancer and/or penetration enhancer, but no crosslinking agent. This results in direct covalent bonds between the adjunct lincosamide and the biological tissue.

Macrolides having at least one hydroxyl group (—OH) capable of forming an ester bond or a phosphodiester bond include: azithromycin, carbomycin, clarithromycin, dirithromycin, erythromycin, josamycin, leucomycins, midecamycins, miokamycin, oleandomycin, primycin, rokitamycin, rosaramicin, roxithromycin, spiramycin and troleandomycin. In some preferred embodiments, the conjugation reagent comprises coupling agent and optionally coupling enhancer and/or penetration enhancer, but no crosslinking agent. This results in direct covalent bonds between the adjunct macrolide and the biological tissue.

Tetracyclines having at least one hydroxyl group (—OH) capable of forming an ester bond or a phosphodiester bond include clomocycline, pipacycline, rolitetracycline. In some preferred embodiments, the conjugation reagent comprises coupling agent and optionally coupling enhancer and/or penetration enhancer, but no crosslinking agent. This results in direct covalent bonds between the adjunct tetracycline and the biological tissue.

Sulfones having at least one hydroxyl group (—OH) capable of forming an ester bond or a phosphodiester bond include: diathymosulfone and glucosulfone. In some preferred embodiments, the conjugation reagent comprises coupling agent and optionally coupling enhancer and/or penetration enhancer, but no crosslinking agent. This results in direct covalent bonds between the adjunct sulfone and the biological tissue.

Other antibiotics having at least one hydroxyl group (—OH) capable of forming an ester bond or a phosphodiester bond include: clofoctol and xibornol.

Sterilization

Before the bioimplant can be implanted in a mammal, especially a human, sterilization must be effected, and such is normally done prior to packaging. The conditions for sterilization are discussed in detail above. In some preferred embodiments, sterilization and conjugation take place in the same process step, and in particular using the same reagent solution comprising sterilizing agent and optionally a sterilizing enhancer and/or a penetration enhancer. In some particularly preferred embodiments, the sterilization solution comprises sterilizing agent and penetration enhancer and optionally a sterilizing enhancer. In some other preferred embodiments, the sterilization solution comprises sterilizing agent, sterilizing enhacer and penetration enhancer. In other embodiments, the sterilization solution comprises sterilizing agent, a crosslinking agent and optionally sterilizing enhancer and/or penetration enhancer.

Preparative Schemes

Following are descriptions of particular schemes for preparing an adjunct conjugated crosslinked and sterilized bioimplant of the invention. The person skilled in the art will recognize that other embodiments may be developed within the scope of the present invention and no disclaimer of such broader invention is intended by presentation of these illustrative examples.

EDC-Assisted Crosslinking/Conjugation

As discussed above, crosslinking of biological tissue and conjugation of adjunct molecules to biological tissue may be carried out in the presence of a variety of crosslinking agents. In some embodiments, the present invention comprises crosslinking of biological tissue with a diamine, such as a $C_4$-$C_{12}$ linear diamine having amine groups with at least about four carbons between them. In particular embodiments, the diamine is water soluble, although non-water soluble or slightly water soluble diamines may be used in some embodiments if a detergent, especially a non-ionic detergent, is used to aid in solubilizing the diamine. Exemplary water soluble diamines contemplated within the scope of the present invention include 1,5-pentane diamine, 1,6-hexane diamine and 1,7-heptane diamine.

In some embodiments, the present invention comprises crosslinking of biological tissue with a diacid, such as a $C_4$-$C_{12}$ linear diacid having carboxyl groups with at least about four carbons between them. In particular embodiments, the diacid is water soluble, although non-water soluble or slightly water soluble diacids may be used in some embodiments if a detergent, especially a non-ionic detergent, is used to aid in solubilizing the diacid. Exemplary water soluble diacids contemplated within the scope of the present invention include 1,5-pentane dicarboxylic acid, 1,6-hexane dicarboxylic acid and 1,7-heptane dicarboxylic acid.

In place of a diacid, there may be substituted a diacid anhydride, such as a $C_4$-$C_{12}$ diacid anhydride having carboxyl groups with at least about four carbons between them. In particular embodiments, the diacid anhydride is water soluble, although non-water soluble or slightly water soluble diacid anhydrides may be used in some embodiments if a detergent, especially a non-ionic detergent, is used to aid in solubilizing the diacid anhydride. Exemplary water soluble diacid anhydrides contemplated within the scope of the present invention include 1,5-pentane dicarboxylic acid anhydride, 1,6-hexane dicarboxylic acid anhydride and 1,7-heptane dicarboxylic acid anhydride.

In place of a diacid or diamine, there may be substituted an amino acid, such as a $C_4$-$C_{12}$ amino acid having a carboxyl group and an amine with at least about four carbons between them. In particular embodiments, the amino acid is water soluble, although non-water soluble or slightly water soluble amino acids may be used in some embodiments if a detergent, especially a non-ionic detergent, is used to aid in solubilizing the amino acid. Exemplary water soluble amino acids contemplated within the scope of the present invention include 5-aminopentan-1-oic acid, 6-aminohexan-1-oic acid and 7-amino-heptan-1-oic acid. Other amino acids may be used as described above.

The diamines form amide bonds between carboxyl groups within the biological tissue, thus linking the carboxyl groups together through an alkylene linker. The diacids and diacid anhydrides form amide bonds with amine (including guanine) groups in proteins within the biological tissue. Likewise, the amine functions of the amino acids form amide bonds with proteinaceous carboxyl groups, while the carboxyl groups of the amino acids form amide bonds with amine groups in the biological tissue.

It is considered advantageous to use a coupling agent to aid in amide bond formation within the biological tissue and between the biological tissue and the. Suitable coupling agents include EDC or N-hydroxysuccinimide (NHS), which enhance amide bond formation when used together with diamine, diacid or amino acid. It is believed that coupling enhancer EDC increases the reaction rate between an amine and a carboxyl group by forming an active intermediate, which lowers the reaction energy barrier of amide bond formation. The formation of an amide bond using EDC is shown in Scheme 1, below.

Scheme 1
EDC-Medicated Amide Bond Formation

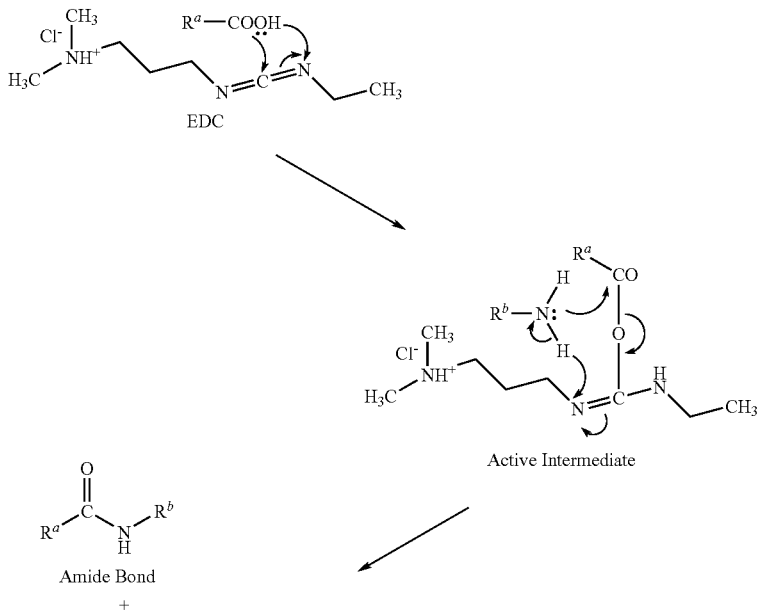

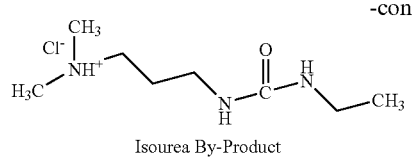

Isourea By-Product

As can be seen in Scheme 1, amide bond formation proceeds through an active intermediate. In particular, a carboxylic acid moiety in a molecule represented by $R^a$—COOH attacks the diimide carbon, forming a relatively unstable o-acylisourea intermediate. Attack of the carbonyl carbon by a free set of electrons in the amine functional group of $R^b$—$NH_2$ results in formation of the amide bond between $R^a$ and $R^b$. In addition, there is formed as a byproduct, a water soluble isourea, which is rinsed away from the biological tissue after conjugation and/or crosslinking.

In some embodiments, $R^a$ represents a protein in a biological tissue and $R^b$ represents an amine-bearing adjunct. In some specific embodiments, $R^a$ represents a protein in the biological tissue having one or more free carboxyls (COOH, or COO—), while $R^b$ represents a protein, peptide, an antibiotic, RNA or DNA having a free amine or a polysaccharide, glycosaminoglycan (GAG) or derivatized to have a free amine. In some embodiments, $R^a$ represents a carboxyl or other acid group on an adjunct and $R^b$ represents a free amine (such as a lysine side chain) on a protein in the biological tissue. In some particular embodiments, $R^a$ is a free carboxyl on a protein, a peptide, an antibiotic or a DNA, RNA or polysaccharide, glycosaminoglycan (GAG) derivatized to have a free carboxyl and $R^a$ represents a free amine on a lysine side chain in a protein in the biological tissue.

In some embodiments, the biological tissue is coupled to the adjunct via a crosslinking agent. In some such embodiments, the acid $R^a$ is a protein, especially a protein in the biological tissue having one or more carboxylic acid moieties (e.g. C-terminal COOH, or carboxyl groups of aspartic and/or glutamic acid residues) available for reaction. In some such embodiments, $R^a$ is be the residue of an acid-bearing adjunct, such as a protein, a peptide or an antibiotic; or it can be a derivatized polysaccharide, glycosaminoglycan (GAG), DNA or RNA. Also, in some such embodiments, $R^a$ can also be an acidic crosslinking agent, such as a diacid, a diacid anhydride or an amino acid. Where $R^a$ is a protein, $R^b$ is, in some embodiments, an amino crosslinking reagent, such as a diamine crosslinking agent. Where $R^a$ is a crosslinking agent, $R^b$ is, in some embodiments, a protein having exposed amine groups (e.g. N-terminal amine or side chain amines of lysine residues). Where $R^a$ represents the residue of an acid-bearing adjunct, $R^b$ is, in some embodiments, an amine-bearing crosslinking or coupling reagent, or $R^b$ can be an amine-bearing protein.

In general, EDC-mediated crosslinking and conjugation are conceptually very similar, as crosslinking, conjugation or both may be carried out using a bifunctional agent (crosslinking/conjugating) capable of forming amide bonds with the desired materials.

In some embodiments, it is considered advantageous to crosslink a biological tissue in one step and conjugate the adjunct molecule to the biological tissue in another step. In some such embodiments, it is considered advantageous to use a homobifunctional linking agent, such as a diamine, a diacid or a diacid anhydride as the crosslinking agent. In some particular embodiments, the homobifunctional linking agent is a diamine, which is used in conjunction with EDC and optionally a coupling enhancer, such as sulfo-NHS or NHS. In such cases, the crosslinking of the biological tissue with a diamine blocks carboxylic acid groups in the tissue proteins, leaving amine groups on the tissue proteins available for conjugation to an adjunct molecule through a suitable conjugation linker. Such conjugation is carried out with a conjugating agent having at least two functional groups. The first functional group should be a functional group capable of reacting with the tissue protein amines to form amide bonds. Suitable conjugation agents include diacids, diacid anhydrides and amino acids, especially such conjugation agents having 4-12 carbons in which the two functional groups are separated by at least four carbon atoms. Where the conjugation agent is a diacid or a diacid anhydride, the adjunct should be one that has, or has been modified to have, at least one free amine for formation of an amide bond with the conjugation agent. Where the conjugation is an amino acid, the adjunct should be one that has, or has been modified to have, at least one carboxylic acid moiety available for formation of an amide bond with the conjugation agent. In any case, conjugation can favorably take place by contacting the adjunct, the crosslinked biological material and the conjugation agent, optionally together with a coupling agent (e.g. EDC or NHS) and/or a coupling enhancer (e.g. NHS or sulfo-NHS).

Figure 2:
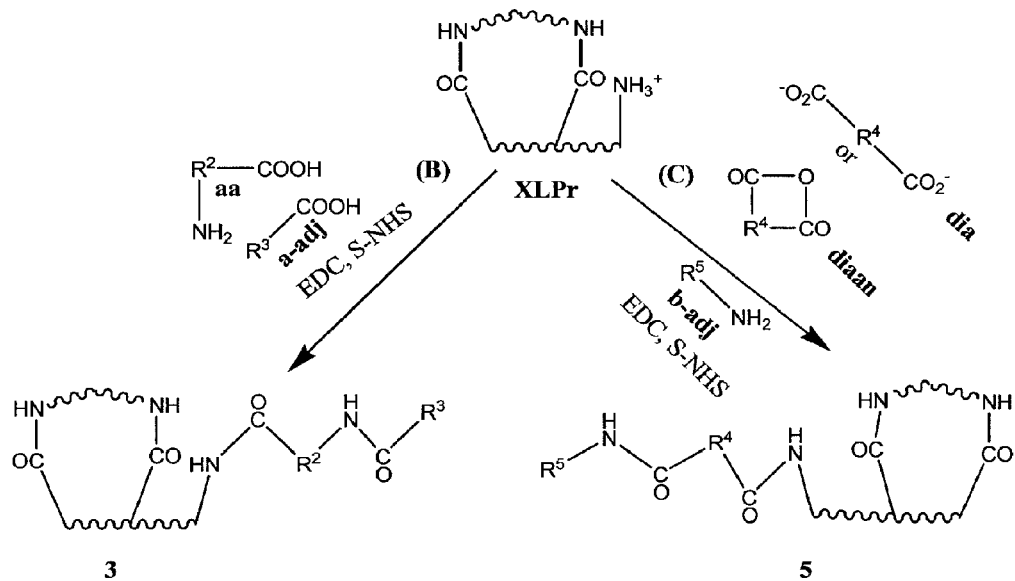
FIG. 2 shows two alternate chemical reaction schemes for preparing a bioimplant of the present invention.

Schemes 2 and 2A, depicted in FIGS. 1 and 2, show how crosslinking followed by adjunct conjugation, is effected in a biological tissue. Referring to Scheme 2 in FIG. 1, in the first step, the protein Pr is shown, having multiple carboxyl moieties and at least one amine moiety. The protein is crosslinked by contacting it with the crosslinking agent diam, which is a diamine, in the presence of a coupling agent (EDC) and a coupling enhancer (sulfo-NHS), which produces the crosslinked protein XLPr.

In a first alternative reaction (A) shown in Scheme 2, the crosslinked protein XLPr is reacted with an adjunct molecule a-adj ($R^1CO_2^-$), having a free carboxyl group, in the presence of coupling agent (EDC) and a coupling enhancer (sulfo-NHS), which produces the adjunct conjugated crosslinked protein 1. The person skilled in the art will recognize that, while $R^1CO_2^-$ may be an adjunct molecule having a free carboxyl in its native state (such as a protein, a peptide or an antibiotic such as one of the penicillins or cephalosporins), it can also represent an adjunct molecule that has been modified to have a carboxyl group, e.g. by reacting an amine-bearing adjunct with a diacid, diacid anhydride, etc., as described above. In some embodiments, the adjunct may have a sulfonate ($SO_3^-$) group instead of a carboxyl group, in which case the expected result will be a sulfonamide bond between the protein and adjunct.

In another alternative reaction (B1) shown in Scheme 2, the crosslinked protein XLPr is reacted with an amino acid conjugating agent aa ($H_2N$—$R^2$—$CO2^-$) in the presence of coupling agent (EDC) and a coupling enhancer (sulfo-NHS), which produces the intermediate crosslinked protein 2. This intermediate 2 is then reacted (B2) with a carboxyl group-bearing adjunct molecule a-adj ($R^3$—$CO_2^-$), to form the adjunct conjugated crosslinked protein 3. The person of skill in the art will recognize that the two reaction steps can be collapsed into a single step, as illustrated in the first reaction sequence (B) illustrated in Scheme 2A of FIG. 2, wherein the crosslinked protein XLPr is reacted with the amino acid aa and the carboxyl bearing adjunct a-adj in the presence of EDC and sulfo-NHS to form the adjunct conjugated crosslinked protein 3.

In yet another alternative reaction shown in Scheme 2, the crosslinked protein XLPr is reacted (C1) with a diacid dia or diacid anhydride diaan in the presence of EDC and sulfo-NHS to form the intermediate 4, which has a free carboxyl group available for further reaction. This free carboxyl group can form an amide bond (C2) with the amine in an adjunct molecule b-adj ($R^5$—$NH_2$), e.g. in the presence of EDC and sulfo-NHS to form the adjunct conjugated crosslinked protein 5. The person skilled in the art will recognize that these two steps can be carried out in the same reaction mixture, as depicted in the second reaction sequence (C) shown in Scheme 2A in FIG. 2.

Figure 4:
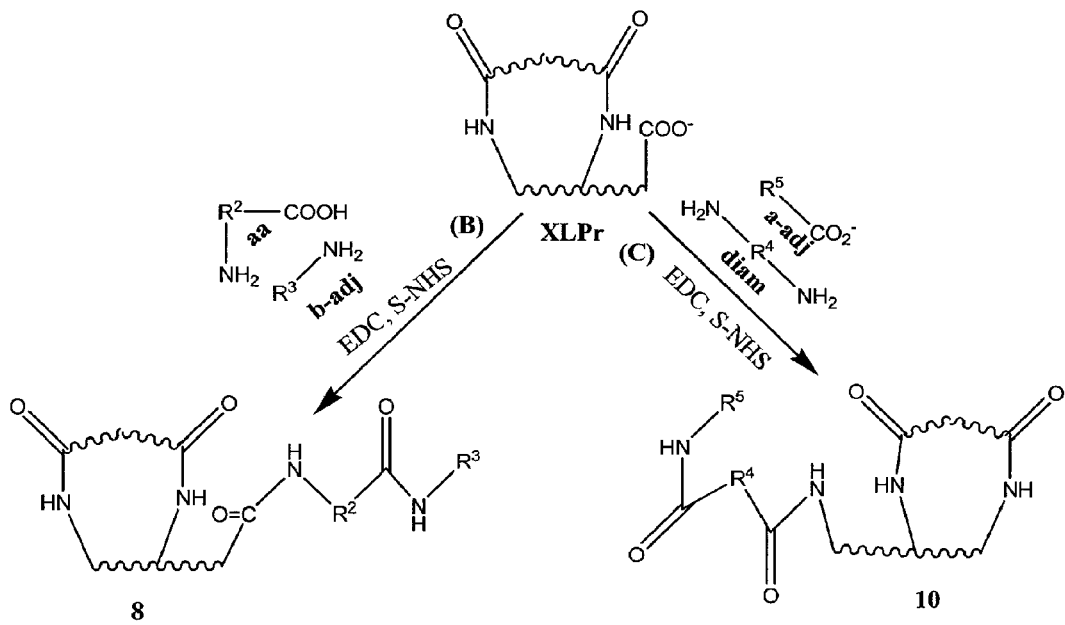
FIG. 4 shows two additional alternate reaction schemes according to the present invention.
Figure 3:
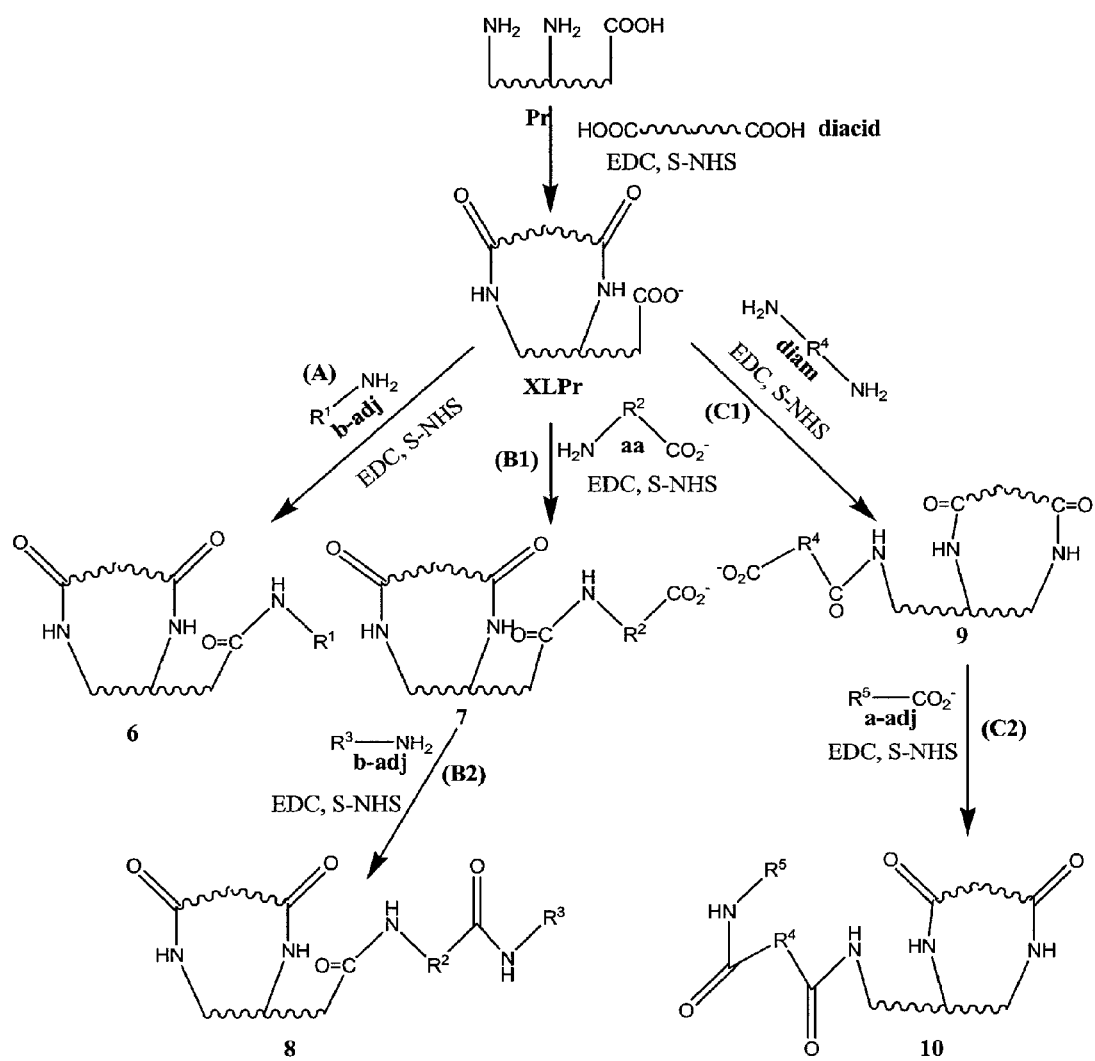
FIG. 3 shows three additional reaction schemes according to the present invention.

Schemes 3 and 3A, depicted in FIGS. 3 and 4, respectively, show how crosslinking followed by adjunct conjugation, is effected in a biological tissue. Referring first to Scheme 3 in FIG. 3, in the first step, the protein Pr is shown, having multiple amine moieties and at least one carboxyl moiety. The protein is then crosslinked by contacting it with the crosslinking agent diacid, which is a diacid (or, as may be appreciated by the person skilled in the art, a dianhydride), in the presence of a coupling agent (EDC) and a coupling enhancer (sulfo-NHS), which produces the crosslinked protein XLPr.

In a first alternative reaction (A) shown in Scheme 3, the crosslinked protein XLPr is reacted with an adjunct molecule b-adj ($R^1$—NH2), in the presence of coupling agent (EDC) and a coupling enhancer (sulfo-NHS), which produces the adjunct conjugated crosslinked protein 6. The person skilled in the art will recognize that, while $R^1$—$NH_2$ may be an adjunct molecule having a free amine in its native state (such as a protein or a peptide), it can also represent an adjunct molecule that has been modified to have an amine group, e.g. by reacting an carboxyl-bearing adjunct (such as a penicillin or cephalosporin) with a diamine as described above.

In another alternative reaction depicted in Scheme 3, the crosslinked protein XLPr is reacted (B1) with an amino acid conjugating agent aa ($H_2N$—$R^2$—$CO2^-$), in the presence of coupling agent (EDC) and a coupling enhancer (sulfo-NHS), which produces the intermediate crosslinked protein 7. This intermediate 7 is then reacted (B2) with an adjunct molecule b-adj ($R^3$—$CO_2^-$), to form the adjunct conjugated crosslinked protein 8. The person of skill in the art will recognize that the two reaction steps can be collapsed into a single step, as illustrated in the first reaction sequence (B) illustrated in Scheme 3A of FIG. 4.

In yet another alternative reaction depicted in Scheme 3, the crosslinked protein XLPr is reacted (C1) with a diamine diam in the presence of EDC and sulfo-NHS to form the intermediate 9, which has a free amine group available for further reaction. This free amine group can form an amide bond (C2) with the carboxyl group in an adjunct molecule a-adj ($R^5$—$NH_2$), e.g. in the presence of EDC and sulfo-NHS to form the adjunct conjugated crosslinked protein 10. The person skilled in the art will recognize that these two steps can be carried out in the same reaction mixture, as depicted in the second reaction sequence (C) in Scheme 3A in FIG. 4.

In preferred embodiments, crosslinking of the tissue and conjugation of the adjunct to the tissue take place in the same step. While a crosslinker may be used in such processes, in some embodiments it is considered preferably to directly conjugate the adjunct to the protein. As proteins in tissues tend to have both free carboxyl groups and free amines, it is considered possible to conjugate adjuncts having at least one carboxyl, at least one amine, or both at least one carboxyl and at least one amine as side chains.

EXAMPLES

The following examples are presented as illustrative, non-limiting embodiments of the present invention. Although these examples are directed toward specific adjuncts, tissue types, and methods of attaching the adjuncts to tissues, the person skilled in the art will recognize that the present invention is not limited to these illustrative examples, and may be practiced with additional adjuncts, tissue types and attachment methods as described herein.

Example 1

Attachment of Glycosaminogycan to Pericardial Tissues

Pericardial tissue was stabilized (cross-linked) using the techniques defined in U.S. Pat. No. 5,447,536, and U.S. patent application Ser. No. 11/276,398, filed Feb. 27, 2006, each of which is expressly incorporated herein by reference in its entirety. Following the cross-linking step, pericardial tissues were exposed to a solution of the glycosaminoglycan (GAG) chondroitin sulfate (0.5%-2.0%) in the presence of EDC for defined periods of time (2 h-overnight). Tissues were subsequently rinsed, and sterilized using the methods described in U.S. Pat. Nos. 6,521,179; 6,506,339; and 5,911,951, each of which is expressly incorporated herein by reference in its entirety. The levels of GAG (glycosaminoglycan) attachment in the tissues were assessed by histological means (differential staining of sections with PAS-Alcian Blue, where GAGs stain blue, while collagen stains pink). The pictures in FIGS. 5A-5C, indicate attachment of GAGs across the pericardial membrane. FIG. 5A shows essentially no blue staining, which is consistent with no GAG being attached to the pericardium. FIG. 5B shows mixed blue and pink staining, which is consistent with partial GAG attachment to the pericardium. FIG. 5C shows nearly complete blue staining, which is indicative of complete GAG attachment to the pericardium.

Example 2

Evaluation of Attachment Steps

The various processing steps (cross-linking, sterilization, etc.,) were then evaluated to determine the tissue processing steps during which the adjuncts could be attached to the tissues. Specifically, this example indicates the various methods of generating a sterile tissue with stably attached adjuncts. A Type 1 collagen sponge that had been subjected to various intermediary processing steps was contacted with a solution of chondroitin sulfate (as an adjunct example) and EDC. FIGS. 6A and 6B show low- and high-magnification histological sections of GAG-attached Type 1 collagen sponge, wherein GAG-attachment was carried out during tissue sterilization. FIG. 7B shows GAG-attached Type 1 collagen sponge, wherein GAG was attached to the tissue during cross-linking. As is apparent from FIGS. 6A, 6B and 7B, attachment of GAG to collagen sponge during sterilization resulted in a diffused attachment, whereas attachment of GAG to tissue during cross-linking produced a close-fitting attachment.

Example 3

Attachment of Adjuncts to Different Tissue Types

In order to demonstrate the applicability of the methods of the present invention to various collagen-based tissue types, three different tissue types were treated in accordance with the present invention. Three different tissue types (pericardium, demineralized cancellous bone, and a collagen sponge made from solubilized Type I collagen) were first cross-linked and subsequently exposed to chondroitin sulfate in the presence of EDC. Tissues were subsequently rinsed, and sterilized using the methods described in U.S. Pat. Nos. 6,521,179; 6,506,339; and 5,911,951. The levels of GAG attachment in the tissues were assessed by histological means (differential staining of sections with PAS-Alcian Blue). The pictures in FIGS. 7A and 7B indicate uniform attachment of GAGs in cancellous bone and collagen sponge tissues.

Example 4

Attachment of Hyaluronic Acid to Biological Tissues

In order to demonstrate that the methods according to the invention may be used to attach various adjuncts to tissues, chondroitin sulfate and hyaluronic acid (HA) were attached to stabilized collagen matrix. The results of attachment of chondroitin sulfate to collagen matrix are discussed above in reference to FIGS. 5A-7B. Hyaluronic acid was attached to collagen matrix essentially as described above in Examples 1-3 for chondroitin sulfate, with hyaluronic acid being substituted for chondroitin sulfate in the attachment step. Histological sections showing hyaluronic acid attached to collagen sponge are shown in FIGS. 8A and 8B, with FIG. 8B representing a high-magnification image of the result shown in FIG. 8A. A histological section of hyaluronic acid attached to pericardium is shown in FIG. 8C.

Example 5

Attachment of IGF-1 to a Collagen Sponge

As a further example of attaching an adjunct to a collagen matrix, IGF-1, which is considered representative of growth factors, was attached to a collagen sponge, essentially by the methods described above with reference to chondroitin sulfate in Examples 1-3. Successful attachment of IGF to collagen sponge was measured using a reverse ELISA assay. In this model, a anti-IGF-1 antibody solution was incubated in contact with a non-IGF-1 attached (control) collagen sponge and an IGF-1 attached collagen sponge. Successful attachment of IGF-1 to the collagen sponge was indicated by a reduction in ELISA signal for the anti-IGF-1 antibody solution after the incubation period. As can be seen in FIG. 8D, the reverse ELISA assay demonstrates a depressed IGF-1 signal for the IGF-1 attached sponge as compared to the control sponge. Thus, the results shown in FIG. 8D demonstrate that IGF-1 was successfully attached to collagen sponge in the presence of EDC.

Example 6

Stability of Adjunct-Modified Tissues

In order to demonstrate the stability of collagenous tissues modified with adjuncts according to the present invention, the stability of chondroitin sulfate attached to crosslinked and sterilized pericardium (prepared essentially as in Example 1, above) was evaluated after 2 months of storage at room temperature. Histological stains specific for GAGs (i.e. PAS-Alcian Blue) indicate the successful retention of the attached GAGs to the crosslinked and sterilized membrane. This demonstrates that the method methods according to the present invention allow one to prepare, sterilize and store collagenous tissues with attached adjuncts that are stable in a hydrated form at room temperature. These results are shown in FIGS. 5A-5C.

Example 7

Biocompatibility of Adjunct-Modified Tissues

The following experiment was conducted to demonstrate the biocompatibility of a tissue prepared by methods according to the invention. In particular, the biocompatibility was evaluated for sterilized collagen sponge having adjunct attached thereto by methods according to the present invention. Cross-linked and sterilized collagen sponge having chondroitin sulfate attached thereto was produced by methods of the present invention and was subjected to cell culture-based assessments. Primary chondrocytes were seeded onto sterilized collagen sponges with or without an adjunct (chondroitin sulfate) attached. The seeded collagen sponges were then incubated in a humidified incubator (37° C., 5% $CO_2$, basal MEM media with 10% fetal calf serum). Viability and metabolic activity of the seeded cells were assessed by the MTT assay at defined time points thereafter. FIG. 9 shows results from a MTT assay, which measures the mitotic activity (and thus the viability) of the attached cells. The results in FIG. 9 demonstrate a recognizable advantage in cell growth, which is conferred by the presence of chondroitin sulfate (with both human and bovine chondrocytes, at 7 days and 14 days of culture, respectively).

FIGS. 10A and 10B show low and high magnification microscopic images, respectively, of the cultures after addition of MTT. Viable cells are stained purple, and the presence of newly synthesized matrix is seen around the cells as a thin fibrinous layer. FIG. 10C is a high magnification image of the sponge showing the appearance of newly synthesized matrix, which has been produced by the seeded chondrocytes.

Example 8

Implantation of Adjunct-Modified Tissues into Live Animals

Stability and compatibility of the tissues with added adjuncts were also tested following implantation in small animals. Briefly, selected samples from the foregoing examples were implanted subcutaneously into rats. Explants were retrieved 4 weeks later, and sections prepared from the explants. These sections were histologically processed and stained to assess the presence of the adjuncts, as well as for the nature of cellular infiltrates. FIG. 11A demonstrates the response from a chondroitin sulfate-modified collagen sponge. Differential staining by PAS-Alcian Blue indicates the continued presence of the GAG even at 4 weeks post implantation. Slow release of the GAG is evident by diffuse appearance of the blue stain in select areas (FIG. 11A). The nature of cellular infiltrates into the samples indicates a biocompatible response from the host (i.e. absence of an overt and active inflammation, appearance of new matrix, and blood vessels between the collagen stands of the tissues (FIG. 11B).

As can be seen from the foregoing examples, the present invention permits the covalent bonding (attachment) of various adjuncts to various types of biological tissues. The biological tissues may be fully-, partially- or un-crosslinked. The adjunct-attached biological tissues are stable over time and are biocompatible. The adjunct-attached biological tissues encourage tissue remodeling, regeneration and healing. Thus, the adjunct-attached biological tissues according to the present invention are useful as implants for a variety of therapeutic uses. The methods of attaching adjuncts to biological tissues according to the invention thus find use in a variety of therapeutic settings.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bioimplant comprising a chemically sterilized biological tissue and at least one heparin adjunct, wherein the heparin adjunct is covalently conjugated to the biological tissue and wherein the chemically sterilized biological tissue is sterilized with a carbodiimide, optionally in the presence of an alkanol, selected from the group consisting of C2-C4 alkanol.

2. The bioimplant of claim 1, wherein the chemically sterilized biological tissue is crosslinked with a carbodiimide, optionally in the presence of a bifunctional crosslinking agent.

3. The bioimplant of claim 1, wherein the biological tissue comprises processed tissue in native form.

4. The bioimplant of claim 1, wherein the biological tissue comprises collagen, purified collagen or solubilized collagen.

5. The bioimplant of claim 1, wherein the heparin adjunct retains at least some of its native activity after it has been conjugated to the biological tissue.

6. The bioimplant of claim 1, wherein the heparin adjunct is adapted to be released in vivo and the heparin adjunct, once release in vivo possesses at least some of its native activity.

7. The bioimplant of claim 1, wherein the chemically sterilized biological tissue is pericardium.

8. The bioimplant of claim 1, wherein the chemically sterilized biological tissue is a sheet of pericardium.

9. The bioimplant of claim 3, wherein said processed tissue in native form comprises decellularized fascia.

* * * * *